(12) United States Patent
Webster

(10) Patent No.: US 6,893,867 B1
(45) Date of Patent: May 17, 2005

(54) MOLECULAR SWITCH FOR REGULATING MAMMALIAN GENE EXPRESSION

(76) Inventor: Keith A. Webster, 740 Allendale Rd., Key Biscayne, FL (US) 33149

(*) Notice: Subject to any disclaimer, the term of this patent is extended or adjusted under 35 U.S.C. 154(b) by 0 days.

(21) Appl. No.: 09/723,326

(22) Filed: Nov. 28, 2000

Related U.S. Application Data
(60) Provisional application No. 60/171,597, filed on Dec. 23, 1999.

(51) Int. Cl.$^7$ .............................................. C12N 15/63
(52) U.S. Cl. ................................................... 435/320.1
(58) Field of Search ....................................... 435/320.1

(56) References Cited

U.S. PATENT DOCUMENTS

| | | |
|---|---|---|
| 5,681,706 A | 10/1997 | Anderson et al. |
| 5,763,217 A | 6/1998 | Cynader et al. |
| 5,834,306 A | 11/1998 | Webster et al. |
| 5,882,914 A | 3/1999 | Semenza |
| 5,942,434 A | 8/1999 | Ratcliffe et al. |
| 6,218,179 B1 | 4/2001 | Webster et al. |

FOREIGN PATENT DOCUMENTS

| | | |
|---|---|---|
| WO | WO 96/20276 | 7/1996 |
| WO | WO 97/13866 | 4/1997 |
| WO | WO 99/05269 | 2/1999 |

OTHER PUBLICATIONS

Awad et al., "Negative Transcriptional Regulation Mediated by Thyroid Hormone Response Element 144 Requires Binding of the Multivalent Factor CTCF to a Novel Target DNA Sequence," The Journal of Biological Chemistry, vol. 274, No. 38, Sep. 17, 1999, pp. 27092–27097.
Baniahmad et al., "t4/tc/AF–2 of the Thyroid Hormone Receptor Relieves Silencing of the Retinotic Acid Receptor Silencer Core Independent of Both t4 Activation Function and Full Dissociation of Corepressors," Molecular and Cellular Biology, vol. 17, No. 8, Aug. 1977, pp. 4259–4271.
Barath et al., "Characterization of a Silencer Element and Purification of a Silencer Protein That Negatively Regulates the Human Adenine Nucleotide Translocator 2 Promoter," The Journal of Biological Chemistry, vol. 274, No. 6, Feb. 1999, pp. 3378–3384.
Bessis et al., "The neuron–restrictive silencer element: A daul enhancer/silencer crucial for patterned expression of a nicotinic receptor gene in the brain," Proc. Natl. Acad. Sci. USA, vol. 94, May 1997, pp. 5906–5911.
Burcin et al., "Negative Protein 1, Which Is Required for Function of the Chicken Lysozyme Gene Silencer in Conjunction with Hormone Receptors, Is Identical tot he Multivalent Zinc Finger Repressor CTCF," Molecular and Cellular Biology, vol. 17, No. 3, Mar. 1997, pp. 1281–1288.
Burcin et al., "Adenovirus–mediated regulable target gene expression in vivo," Proc. Natl. Acad. Sci. USA, vol. 96, Jan. 1999, pp. 355–360.

Cao et al., "A novel approach for inducing enhanced and selective transgene expression in hepatocellular–carcinoma cells," International Journal of Cancer, vol. 87, Issue 2, Jun. 15, 2000, pp. 247–252.
Edelman et al., "Synthetic promoter elements obtained by nucleotide sequence variation and selection for activity," PNAS, vol. 97, No. 7, Mar. 28, 2000, pp. 3038–3043.
Freundlieb et al., "A Tetracycline Controlled Activation/Respression System with Increased Potential for Gene Transfer into Mammalian Cells," The Journal of Gene Medicine, vol. 1, 1999; pp. 4–12.
Imagawa et al., "CTG Triplet Repeat in Mouse Growth Inhibitory Factor/Metallothionein III Gene Promoter Represses the Transcriptional Activity of the Heterologous Promoters," The Journal of Biological Chemistry, vol. 270, No. 36, Sep. 8, pp. 20898–20900.
Jhaveri et al., "Contribution of proximal promoter elements to the regulation of basal and differential glutathione S–transferase P1 gene expression in human breast cancer cells," Biochimica et Biophyhsica Acta, 1998, pp. 179–190.
Kallunki et al., "The neural restrictive silencer element can act as both a repressor and enhancer of L1 cell adhesion molecule gene expression during postnatal development," Proc. Natl. Acad. Sci. USA, vol. 95, Mar. 1988,vol. 1396, pp. 3233–3238.
Koenigsberger et al., "Differential regulation by multiple promoters of the gene encoding the neuron–restrictive silencer factor," PNAS, vol. 97, No. 5, Feb. 29, 2000, pp. 2291–2296.
Li et al., "Identification of a functional silencer element involved in neuron–specific expression of the synapsin I gene," Proc. Natl. Acad. Sci. USA, vol. 90, Feb. 1993, pp. 1460–1464.
Malone et al., "Silencer elements controlling the B29 (Igβ) promoter are neither promoter–nor cell–type–specific," Proc. Natl. Acad. Sci. USA, vol. 94, Nov. 1997, pp. 12314–12319.

(Continued)

Primary Examiner—Terry McKelvey
(74) Attorney, Agent, or Firm—Ruden, McClosky; Stanley A. Kim

(57) ABSTRACT

Expression vectors are disclosed that are comprised of (a) one or more silencer elements and conditionally inducible elements to form silencer-inducible regions and (b) promoters in operative linkage upstream of at least one expressed region. The expression vector thereby regulates expression of at least one downstream region by conditional silencing in which an expressed DNA region of a gene is transcribed to produce RNA transcripts, which may or may not be translated to produce polypeptides. Genetically engineered mammalian cells and non-human mammals can be made using such expression vectors through transfection and transgenesis techniques. Moreover, processes of making and using the aforementioned products are disclosed (e.g., the expression vector may be used diagnostically, therapeutically, or prophylactically).

13 Claims, 3 Drawing Sheets

OTHER PUBLICATIONS

Malone et al., "An Upstream Oct.–1 and Oct–2–Binding Silencer Governs B29 (Igβ) Gene Expression[1]," The Journal of Immunology, vol. 164, 2000, pp. 2550–2556.

Millecamps et al., "Neuron–restrictive silencer elements mediate neuron specificity of adenoviral gene expression," Nature Biotechnology, vol. 17, Sep. 1999, pp. 865–869.

Nabel, "Development of optimized vectors for gene therapy," Proc. Natl. Acad. Sci. USA, vol. 96, Jan. 1999, pp. 324–326.

Nagasawa et al., "Oct.–1, silencer sequence, and GC box regulate thyroid hormone receptor β1 promoter," Molecular and Cellular Endocrinology, vol. 130, 1997, pp. 153–165.

Naruse et al., "Neural restrictive silencer factor recruits mSin3 and histone deacetylase complex to repress neuron–specific target genes," PNAS, vol. 96, No. 24, Nov. 23, 1999, pp. 13691–13696.

Natesan et al., "A general strategy to enhance the potency of chimeric transcriptional activators," PNAS, vol. 96, No. 24, Nov. 23, 1999, pp. 13898–13903.

Nourbakhsh et al., "The Transcriptional Silencer Protein NRF: A Repressor of NF–kB Enhancers," Immunobiol., vol. 198, 1997, pp. 65–72.

Nourbakhsh et al., "Constitutive silencing of IFN–β promoter is mediated by NRF (NF–kB–repressing factor), a nuclear inhibitor of NF–kB," The EMBO Journal, vol. 18, No. 22, 1999, pp. 6415–6425.

Osada et al., "CCAAT/Enhancer–binding Proteins α and β Interact with the Silencer Element in the Promoter of Glutathione S–Transferase P Gene during Hepatocarcinogenesis," The Journal of Biological Chemistry, vol. 270, No. 52, Dec. 29, 1995, pp. 31288–31293.

Osada et al., "Nuclear Factor 1 Family Proteins Bind to the Silencer Element in the Rat Glutathione Transferase P Gene," J. Biochem, vol. 121, 1997, pp. 355–363.

Osada et al., "Expression, DNA–binding specificity and transcriptional regulation of nuclear factor 1 family proteins from rat," Biochem. J., vol. 342, 1999, pp. 189–198.

Pierce et al., "Silencing of the Expression of the Immunoglubulin Kappa Gene in Non–B Cells," Molecular and Cellular Biology, vol. 11, Mar. 1991, pp. 1431–1437.

Porter, "Controlling your losses: conditional gene silencing in mammals," TIG, vol. 14, No. 2, Feb. 1998, pp. 73–79.

Quinn, "Neuronal–Specfic Gene Expression—The Interaction of Both Positive and Negative Transcriptional Regulators," Progress in Neurobiology, vol. 50, 1996, pp. 363–379.

Saez et al., "Inducible gene expression in mammalian cells and transgenic mice," Current Opinion in Biotechnology, vol. 8, 1997, pp. 608–616.

Thrower et al., "Regulation of a Human Cytomegalovirus Immediate–Early Gene (US3) by a Silencer–Enhancer Combination," Journal of Virology, vol. 70, No. 1, Jan. 1996, pp. 91–100.

Weber et al., "Identification of a Novel Repressive Element That Contributes to Neuron–Specific Gene Expression," The Journal of Neuroscience, vol. 17, No. 20, Oct. 15, 1992, pp. 7583–7593.

Webster, "One–Step, Two–Step Regulation of Therapeutic Genes," The Scientist, vol. 13, No. 9, Apr. 26, 1999, p. 13.

Wolfe et al., "Binding of Nuclear Proteins to an Upstream Element Involved in Transcriptional Regulation of the Testis–Specific Histone H1t Gene," Journal of Cellular Biochemistry, vol. 75, 1999, pp. 555–565.

Wolfe et al., "Localization of Upstream Elements Involved in Transcriptional Regulation of the Rat Testis–Specific Histone H1t Gene in Somatic Cells," Biology of Reproduction, vol. 61, 1999, p. 1005–1011.

Ye et al., "Regulation of a Cell Type–specific Silencer in the Human Interleukin–3 Gene Promoter by the Transcriptional Factor YY1 and an AP2 Sequence–recognizing Factor," The Journal of Biological Chemistry, vol. 274, No. 38, Sep. 17, 1999, pp. 26661–26667.

Binley K, Iqball S, Kingsman A, Kingsman S, Naylor S. 1999. An adenoviral vector regulated by hypoxia for the treatment of ischaemic disease and cancer, Gene Ther. 6(10):1721–7.

Koshikawa N, Takenaga K, Tagawa M, Sakiyama S. 2000. Therapeutic efficacy of the suicide gene driven by the promoter of vascular endothelial growth factor gene against hypoxic tumor cells. Cancer Res. 60(11):2936–41.

Modlich U, Pugh CW, Bicknell R. 2000. Increasing endothelial cell specific expression by the use of heterologous hypoxic and cytokine–inducible enhancers. Gene Ther. 7(10):896–902.

Salnikow K, Costa M, Figg WD, Blagosklonny MV. 2000 Hyperinducibility of hypoxia–responsive genes without p53/p21–dependent checkpoint in aggressive prostate cancer. Cancer Res. 60(20):5630–4.

Shibata T, Giaccia AJ, Brown JM. 2000. Development of a hypoxia–responsive vector for tumor–specific gene therapy. Gene Ther. 7(6):493–8.

Millecamps S, Kiefer H, Navarro V, Geoffroy MC, Robert JJ, Finiels, F, Mallet J, Barkats M. 1999. Neuron–restrictive silencer elements mediate neuron specificity of adenoviral gene expression. Nat. Biotechnol. 17(9):865–9.

Coulson et al., "Arginine Vasopressin Promoter Regulation Is Mediated by a Neuron–restrictive Silencer Element In Small Cell Lung Cancer," Cancer Research, 59: 5123–5127, 1999.

Shimojo et al., "Protein Kinase A Regulates Cholinergic Gene Expression in PC12 Cells: REST4 Silences the Silencing Activity of Neuron–Restrictive Silencer Factor/REST," Molecular and Cellular Bio., 19: 6788–6795, 1999.

Avisar et al., "A Silencer Element in the Regulatory Region of Glutamine Synthetase Controls Cell Type–specific Repression of Gene Induction by Glucocorticoids," The Journal of Biological Chemistry, 274: 11399–11407, 1999.

Timmusk et al., "Brain–derived Neurotrophic Factor Expression in Vivo is under the Control of Neuron–restrictive Silencer Element," The Journal of Biological Chemistry, 274: 1078–1084, 1999.

Kallunki et al., "The neural restrictive silencer element can act as both a repressor and enhancer of L1 cell adhesion molecule gene expression during postnatal development," Proc. Natl. Acad. Sci. USA, 95: 3233–3238, 1998.

Palm et al., "Neuronal Expression of Zinc Finger Transcription Factor REST/NRSF/XBR Gene," The Journal of Neuroscience, 18: 1280–1296, 1998.

Kallunki et al., "Tissue–specific Expression of the L1 Cell Adhesion Molecule Is Modulated by the Neural Restrictive Silencer Element," The Journal of Cell Biology, 138: 1343–1354, 1997.

Pepitoni et al., "Structure of the m1 Muscarinic Acetylcholine Receptor Gene and Its Promoter," The Journal of Biological Chemistry, 272: 17112–17117, 1997.

Mieda et al., "Expression of the Rat m4 Muscarinic Acetylcholine Receptor Gene Is Regulated by the Neuron-restrictive Silencer Element/Repressor Element 1," The Journal of Biological Chemistry, 272: 5854–5860, 1997.

Lonnerberg et al., "Cell Type-specific Regulation of Choline Acetyltransferase Gene Expression," The Journal of Biological Chemistry, 271: 33358–33365, 1996.

Schoenherr et al., "Identification of potential target genes for the neuron-restrictive silencer factor," Proc. Natl. Acad. Sci. USA, 93: 9881–9886, 1996.

Wood et al., "Neural Specific Expression of the m4 Muscarinic Acetylocholine Receptor Gene Is Mediated by a RE1/NRSE-type Silencing Element," The Journal of Biological Chemistry, 271: 14221–14225, 1996.

Schoch et al., "Neuron-specific Gene Expression of Synapsin I," The Journal of Biological Chemistry, 271: 3317–3323, 1996.

Kallunki et al., "Silencer Elements Modulate the Expression of the Gene for the Neuron-Glia Cell Adhesion Molecule, Ng-CAM," The Journal of Biological Chemistry, 270: 21291–21298, 1995.

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 1
tgtcacgtcc tgcacgacgt a                                            21

<210> SEQ ID NO 2
<211> LENGTH: 22
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 2
cttcagcacc gcggacagtg cc                                           22

<210> SEQ ID NO 3
<211> LENGTH: 22
<212> TYPE: DNA
<213> ORGANISM: Artificial
<220> FEATURE:
<223> OTHER INFORMATION: Description of Artificial Sequence: Mammalian
      gene regulatory sequence
```

```
<400> SEQUENCE: 3
tgtccattcc tgcacgacgt ac                                                  22

<210> SEQ ID NO 4
<211> LENGTH: 22
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 4
cttcagcacc gcttacagtg cc                                                  22

<210> SEQ ID NO 5
<211> LENGTH: 43
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 5
cttcagcacc gcggacagtg cctgtcacgt cctgcacgac gta                           43

<210> SEQ ID NO 6
<211> LENGTH: 86
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 6
cttcagcacc gcggacagtg cctgtcacgt cctgcacgac gtacttcagc accgcggaca         60
gtgcctgtca cgtcctgcac gacgta                                              86

<210> SEQ ID NO 7
<211> LENGTH: 123
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 7
cttcagcacc gcggacagtg cctgtcacgt cctgcacgac ttcagcaccg cggacagtgc         60
ctgtcacgtc ctgcacgact tcagcaccgc ggacagtgcc tgtcacgtcc tgcacgacgg        120
tac                                                                      123

<210> SEQ ID NO 8
<211> LENGTH: 33
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 8
cttcagcacc gcggacagtc acgtcctgca cga                                      33
```

```
<210> SEQ ID NO 9
<211> LENGTH: 129
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 9
cttcagcacc gcttacagtg cctgtcacgt cctgcacgac gtacttcagc accgcttaca      60
gtgcctgtca cgtcctgcac gacgtacttc agcaccgctt acagtgcctg tcacgtcctg     120
cacgacgta                                                              129

<210> SEQ ID NO 10
<211> LENGTH: 132
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 10
cttcagcacc gcggacagtg cctgtccatt cctgcacgac gtaccttcag caccgcggac      60
agtgcctgtc cattcctgca cgacgtacct tcagcaccgc ggacagtgcc tgtccattcc     120
tgcacgacgt ac                                                          132

<210> SEQ ID NO 11
<211> LENGTH: 116
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 11
cttcagcacc gcggacagtt gaggggactt tcccaggctt cagcaccgcg gacagttgag      60
gggactttcc caggcttcag caccgcggac agttgagggg actttcccag gcgtac         116

<210> SEQ ID NO 12
<211> LENGTH: 116
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 12
cttcagcacc gcttacagtt gaggggactt tcccaggctt cagcaccgct tacagttgag      60
gggactttcc caggcttcag caccgcttac agttgagggg actttcccag gcgtac         116

<210> SEQ ID NO 13
<211> LENGTH: 199
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 13
cttcagcacc gcggacagtt gacacgatca cctcccatta aggagagaga tctccttcag      60
caccgcggac agttgacacg atcacctccc attaaggaga gagatctcct tcagcaccgc     120
```

-continued

```
ggacagttga cacgatcacc tcccattaag gagagagatc tccttcagca ccgcggacag      180
ttgaggggac tttcccagg                                                  199

<210> SEQ ID NO 14
<211> LENGTH: 162
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 14
cttcagcacc gcggacagtt gagcttcggg gcttttgcac tcgtcccggc tctacttcag       60
caccgcggac agttgagctt cggggctttt gcactcgtcc cggctctact tcagcaccgc      120
ggacagttga gcttcggggc ttttgcactc gtcccggctc ta                         162

<210> SEQ ID NO 15
<211> LENGTH: 52
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 15
ctggccttat ctccggctgc acgttgcctg ttggtgacta ataacacaat aa               52

<210> SEQ ID NO 16
<211> LENGTH: 162
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 16
cttcagcacc gcggacagtt gacacgatca cctcccatta aggagagaga tctccttcag       60
caccgcggac agttgacacg atcacctccc attaaggaga gagatctcct tcagcaccgc      120
ggacagttga cacgatcacc tcccattaag gagagagatc tc                         162

<210> SEQ ID NO 17
<211> LENGTH: 38
<212> TYPE: DNA
<213> ORGANISM: Artificial
<220> FEATURE:
<223> OTHER INFORMATION: Description of Artificial Sequence: Mammalian
      gene regulatory sequence

<400> SEQUENCE: 17
cttcagcacc gcggacagtg cctgtcacgt cctgcacg                               38
```

MOLECULAR SWITCH FOR REGULATING MAMMALIAN GENE EXPRESSION

CROSS-REFERENCE TO RELATED APPLICATION

This application claims priority benefit of provisional U.S. Appln. Ser. No. 60/171,597, filed Dec. 23, 1999.

BACKGROUND OF THE INVENTION

1. Field of the Invention

The present invention relates to the regulation of mammalian gene expression.

2. Description of Related Art

Gene transfer involves the transfer of foreign genetic material into a cell such that the foreign material is expressed. This process is used in applications such as, for example: gene therapy, production of recombinant biologicals, genetic diagnosis, and drug screening. But despite recent reports of success in the most challenging of these fields, in vivo gene therapy of human diseases (Kay et al., 2000; Cavazzano-Calvo et al., 2000), the construction of new expression vectors has occupied the attention of the many workers eager to achieve high levels of gene expression in a regulated manner (reviewed in Agha-Mohammadi and Lotze, 2000).

In most cases, the ultimate goal of gene transfer is to introduce an expression vector that provides for production of a gene product for a period sufficient for a therapeutic or prophylactic effect, which period may be relatively short (e.g., a few hours to a few days) or may be for long periods (e.g., several weeks to one or more years). One important aspect of gene-based therapy could involve regulating expression in such a manner that gene expression is restricted spatially and temporally to cells or tissues that are affected by a disease. Such regulation requires that the gene be delivered to the target cell or tissue in a substantially latent state, so that it does not change or significantly affect the phenotype of the target in the absence of disease. Where and when the disease is active, it would be desirable that the latent gene should then be induced (e.g., spatially, temporally, or both) in a manner that will counteract disease symptoms and, conversely, ceases expression as the disease symptoms subside. To simplify, this requires that the gene be regulated by a tight on/off switch that can respond to an intrinsic disease-related stimulus.

A critical feature of such regulated gene expression is called the silencer-inducer ratio: expression of the foreign gene measured under inducing conditions divided by the amount of expression without induction (i.e., basal expression). This ratio should be high (e.g., at least about 25- to 1000-fold) and sufficiently regulatable by appropriate control of inducing conditions. Another critical feature is substantially silenced (or repressed) gene expression in the non-induced, disease-free state.

This requirement for a tight on/off switch in regulating expression of a foreign gene is widely acknowledged and the absence of such regulation is considered to be one of the major limitations for many gene transfer applications. Regulated expression of foreign genes, both positive and negative, has been described in prokaryotes (e.g., the Lac operon) and in mammals (e.g., Tet-repressor and activator, progesterone or ecdysone receptor) (reviewed in Agha-Mohammadi and Lotze, 2000). Each of these systems involves binding of an extrinsic modulator to a protein involved in transcription: tetracycline or doxycycline in the Tet regulatory system; RU486 or rapamycin in the progesterone and FKBP regulatory systems, respectively. The latter two systems require multiple vectors to deliver the target gene and the different regulatory components. In all of these systems, allosteric changes determine the DNA binding affinities of positive- and negative-acting transcriptional factors and thereby control an on/off switch (Freundlieb et al., 1999). Unlike the invention, however, these systems do not provide spatial regulation within a tissue or responsiveness to a disease state by an intrinsic factor (e.g., hypoxia or stress) acting on endogenous transcriptional factors (e.g., hypoxia inducible factors or NF-κB transcription factors, respectively). A system of regulated expression has been engineered in yeast where allosteric activation (i.e., phosphorylation) of positive- or negative-acting factors activate or repress transcription (Lee and Gross, 1993). These systems provide a solution to the problem of providing a tight on/off switch for regulated expression by using allosteric binding and an extrinsic modulator to control activity of a promoter. As compared to the invention described herein, these systems are all dissimilar in mechanism because this invention uses disease-responsive intrinsic factors to mediate spatial as well as temporal reversible repression, but does not depend upon allosteric binding. Therefore, allosteric regulatory systems do not teach or suggest the invention.

SUMMARY OF THE INVENTION

The present invention relates to the regulation of mammalian gene expression in a cell using at least (a) one or more silencer elements and (b) one or more conditionally inducible elements responsive to one or more instrinsic transcription factors associated with a disease to form a silencer-inducible region that modifies transcriptional activity of a promoter upstream of an expressed region under appropriate conditions. Expression vectors comprised of silencer-inducible region, promoter, and at least one expressed region can thereby regulate expression (i.e., biological activity of RNA corresponding to a product transcribed from an expressed region of the gene or polypeptide corresponding to a product encoded by an expressed region of the gene) by conditional silencing, and confine such expression to cells or portions of tissue that are affected by a disease condition. The silencer elements used may comprise a neuron restrictive silencer (NRS) element bound by neuron restrictive silencer (NRS) transcription factor.

An object of this invention is to tightly regulate mammalian gene expression (i.e., biological activity of RNA corresponding to products transcribed from an expressed region of the gene or polypeptides corresponding to product encoded by an expressed region of the gene) by conditional silencing. Preferably, gene expression is regulated by disease-associated intrinsic factors (e.g., ischemia and other hypoxic conditions, inflammation and other stress conditions).

An expression vector is disclosed that is a polynucleotide comprised of one or more silencer elements, one or more conditionally inducible elements, which are formed into a silencer-inducible region, and promoter in operative linkage upstream of at least one expressed region. The number of silencer elements and conditionally inducible elements are independently selected, usually less than ten of each, and are formed as a homomultimer (i.e., repeats of the same silencer or conditionally inducible element) or a heteromultimer (i.e., mixture of different silencer or conditionally inducible elements, or variations thereof. The expression vector thereby regulates transcription of the one or more downstream regions by conditional silencing in which an expressed DNA region of a gene is transcribed to produce a gene product, e.g., RNA transcripts, polypeptides, and the like.

Expression is inducible through transcription factor binding to the conditionally inducible elements that positively affect transcription by the promoter, and the presence of silencer elements in close apposition to the conditionally inducible elements such that basal activity of the promoter to transcribe a downstream expressed region is conditionally silenced. Preferably, the transcription factor is responsive to an intrinsic factor associated with disease. The ratio of gene expression measured with induction divided by gene expression measured without induction (i.e., the silencer-inducer ratio) is high. Preferably, the silencer-inducer ratio is at least about 25 or 50; more preferably, at least 100 or 500; and even more preferably, at least 1000.

Genetically engineered mammalian cells and non-human mammals can be made using such expression vectors through transfection, infection, and transgenesis techniques.

Furthermore, processes of making and using the aforementioned products are disclosed (e.g., the expression vector may be used diagnostically, therapeutically, or prophylactically or to make models of human disease).

These and other aspects of the present invention will be apparent to a person skilled in the art from the following description.

DESCRIPTION OF THE INVENTION

Definitions

Figure 1:
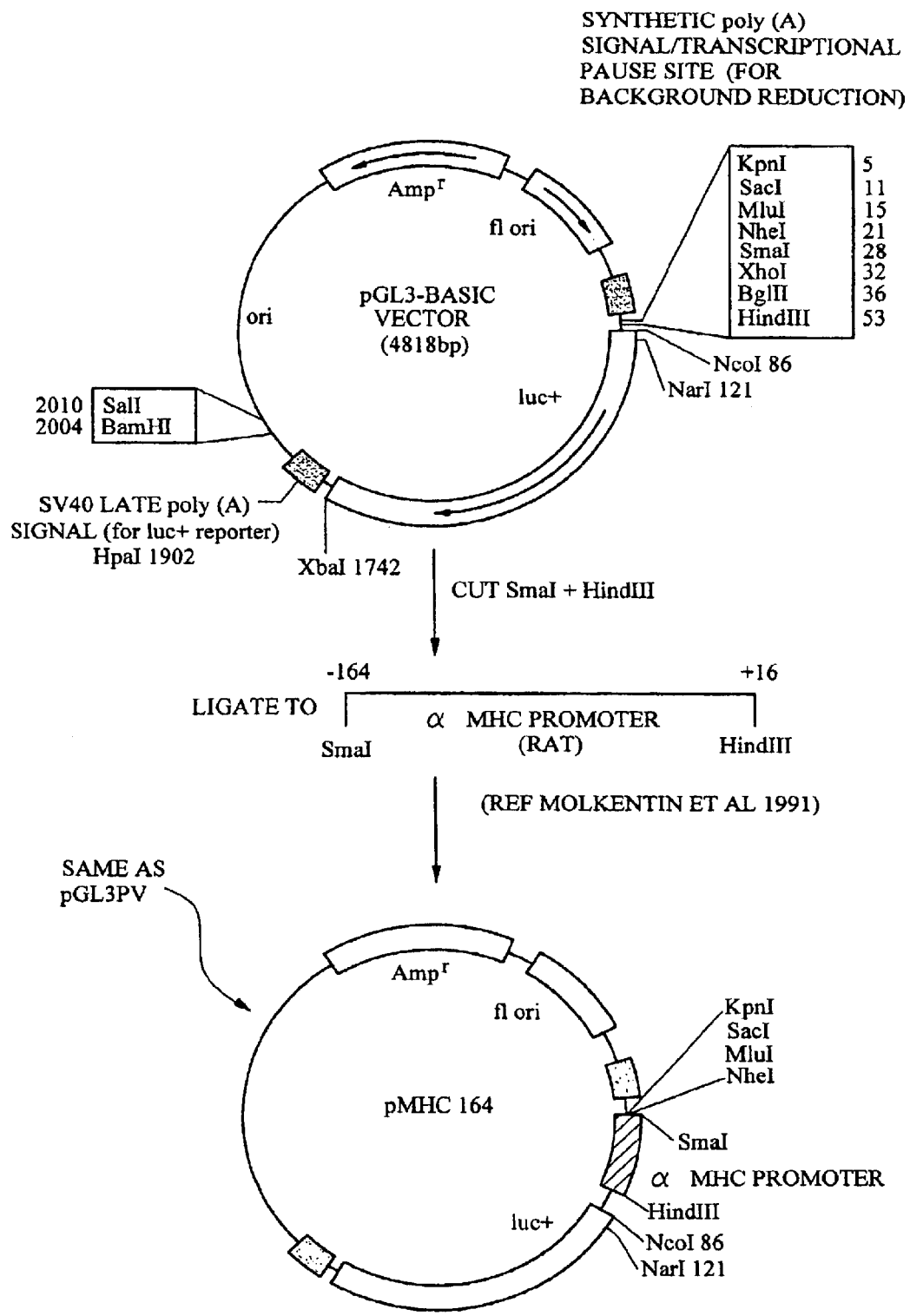
FIG. 1 depicts construction of pMHC164.

A "recombinant" polynucleotide results from ligation or otherwise joining heterologous regions. Recombination may be genetically engineered in vitro with at least partially purified enzymes (e.g., amplification, transcription, or replication); synthesized by manual or automated chemical techniques (e.g., phosphodiester or phosphotriester chemistry); or accomplished in vivo by enzyme catalyzed, site specific recombination (e.g., integrase or RAG recombinase systems) or homologous recombination. The meaning of "heterologous" will, of course, depend on its context. For example, ligation of heterologous regions to form a chimera means that those regions are not found colinear in the same organism. Ligation of regions, at least one derived from human and another derived from a non-human species, are heterologous because they are derived from different species. In a further example, transfection of an expression vector into a heterologous host cell or transgenesis of a heterologous non-human organism means that the expression vector is not found in the cell's or organism's genome in nature.

An "isolated" product is at least partially purified from a chemical reaction for an artificially synthesized polymer of nucleotides or amino acid or from its cell of origin (e.g., human, non-human mammal, or other eukaryote; insect or other invertebrate; plant; yeast, mold, or other fungus; bacterium or other prokaryote) for natural polymers and genetically engineered polymers. For example, as compared to a lysate of the cell of origin, the isolated product is at least 50%, 75%, 90%, 95% or 98% purified from other chemically similar solutes (e.g., nucleic acids for polynucleotides, proteins for polypeptides). For a chemically synthesized polymer of nucleotides or amino acids, purity is determined by comparison to prematurely terminated or blocked products and may, as a practical matter, be considered isolated without purification with high fidelity synthesis. Purification may be accomplished by biochemical techniques such as, for example, cell fractionation, centrifugation, chromatography, and electrophoresis. Generally, solvent (e.g., water) and chemicals like buffers and salts are disregarded when calculating purity. Cell products can be isolated by positive or negative selection, limiting dilution, or sorting according to whether an expression vector was introduced into a host cell. Cell or gene cloning is often used to isolate the desired product. Thus, a polynucleotide can be considered "isolated" when it is contained in a virus particle or transfected cell as a substantially homogeneous population obtained by cloning.

An "expression vector" is a recombinant polynucleotide that is in chemical form either a deoxyribonucleic acid (DNA) or a ribonucleic acid (RNA). The physical form of the expression vector may also vary in strandedness (e.g., single-stranded or double stranded) and topology (e.g., linear or circular). It should be understood, however, that the expression vector is preferably a double-stranded deoxyribonucleic acid (dsDNA) or is converted into a dsDNA after introduction into a cell (e.g., insertion of a retrovirus into a host genome as a provirus). The expression vector may be associated with proteins and other nucleic acids in a carrier (e.g., packaged in a viral particle) or it may be comprised of modified nucleotides (e.g., methylated nucleotides). The expression vector may be based on a shuttle vector such as, for example, a phagemid, plasmid, bacteriophage or virus, cosmid, bacterial artificial chromosome (BAC), or yeast artificial chromosome (YAC). The vector may be encapsulated within an adeno-associated virus particle. Although not a limiting aspect of the invention, the length of the expression vector may conveniently be between 100 and 1,000,000 nucleotides long or, more preferably, between 1000 and 100,000 nucleotides long or, even more preferably, between 5,000 and 50,000 nucleotides long, with or without integration into a host genome.

An expression vector in accordance with the present invention is comprised of at least one silencer element, at least one conditionally inducible element, and at least one promoter which are in operative linkage to provide for regulation of at least one expressed region. Preferably, one or more of the silencer elements and one or more of the conditionally inducible elements are heterologous to each other; the silencer-inducible regions formed from silencer and conditionally inducible elements act to conditionally silence expression in a mammalian cell or tissue, and regulate such expression in a restricted spatial and temporal pattern; and intrinsic factors associated with disease (e.g., ischemia and other hypoxic conditions, inflammation and other stress conditions) are used to regulate expression instead of extrinsic factors (e.g., drugs, recombinant trans-acting factors such as recombinant polypeptides, and the like) acting by an allosteric mechanism.

Thus, the expression vector regulates gene expression by "conditional silencing" through a non-allosteric mechanism:

reversible, mutually exclusive binding of negative-acting transcription factor to the silencer element and positive-acting transcription factor to the conditionally inducible elements. In mammalian cells or tissues, the desired result is tight regulation of an expressed DNA region of the gene that is transcribed to produce a single class or multiple different classes of RNA transcripts, which then may or may not be translated to produce a single class or multiple different classes of polypeptides. For example, the biological activity of the gene may be regulated at the level of the transcripts per se (i.e., inducible RNA activity) and/or the polypeptides (i.e., inducible protein activity). dsRNA and ribozyme molecules are examples of transcripts with RNA activity. Examples of protein activity include affinity binding, enzymatic activity, signal transduction resulting from binding between receptors and their cognate ligands, and other physiological responses.

The number of silencer elements and conditionally inducible elements are independently at least two, three, four, five, six, or more as a homomultimer (i.e., repeats of the same silencer or conditionally inducible element) or a heteromultimer (i.e., mixture of different silencer or conditionally inducible elements, or. variations thereof. The types and numbers of silencer elements and conditionally inducible element in the expression vector may be varied; it is expected, however, that the silencer-inducer ratio will generally increase and eventually plateau in direct relationship with the number of elements for most, if not all, types of element. If the sequence of an element is not dyad symmetric, then there might be a preferred orientation of the element with respect to the rest of the expression vector (e.g., a promoter) but the difference in silencer-inducer ratios produced thereby will probably be insubstantial. If the silencer-inducible region functions as an "enhancer" then orientation and separation of the enhancer relative to the promoter will not be a critical determinant in operation of the invention.

The distance between a transcriptional start site of the promoter and the nearest sequence of the most proximal silencer-inducible region may be at most 500, 1000, 1500, 2000 or 2500 nucleotides. But as noted above, although this distance is about 100 to about 300 nucleotides for the expression vectors shown in the examples, it is not believed to be critical to obtaining the advantages of the invention. Note that some promoters, especially those lacking TATA and CAAT consensus sequences, may have multiple transcriptional sites that are responsible for at least 10% of the total initiation of transcription. This distance might be varied to maximize the silencer-inducer ratio. Thus, the effect on the silencer-inducer ratio of a spacer sequence between promoter and silencer-inducible region will usually depend on the number of nucleotides in the spacer sequence and not the identity of those nucleotides' bases. Mutational analysis of the spacer sequence would be expected to confirm the boundaries of a promoter and a silencer-inducible region because a change in the base of a spacer sequence should result in an insubstantial difference in the silencer-inducer ratio. Otherwise, the length of the promoter or silencer-inducible region (whichever is nearest) may have to be considered enlarged, and the spacer sequence equivalently shortened.

Potentially more important for conditional silencing is the distance separating silencer elements and conditionally inducible elements. Preferably, their separation is restricted so there is interference between the binding of negative-acting transcription factors to the silencer elements and the binding of positive-acting transcription factors to the conditionally inducible elements. A separation of more than 500 bases between silencer element and conditionally inducible element eliminated conditional silencing (Example 1), but conditional silencing correlated directly with displacement of proteins binding to the silencer element by different proteins binding to the conditionally inducible element with a separation of only about 50 bases (Example 3). Other arrangements with greater separations are possible within the context of the invention in circumstances with DNA bending or long distance interactions that affect binding to DNA sites in the silencer and conditionally inducible elements.

Silencer and conditionally inducible elements within a silencer-inducible region can be arranged such that the silencer element and the conditionally inducible element are separated in the expression vector by about 50 or 75 bases or less; and may be separated by about 100 or 150 bases to about 200 or 300 bases; and may be separated by about 500 or 1000 bases or more. As discussed above, mutational analysis can be used to confirm the length of the silencer-inducible region. For example, at least some mutations in transcription factor binding sites of the silencer elements and the conditionally inducible elements would be expected to change the silencer-inducer ratio, although no change in that ratio would be expected in bases located between binding sites or elements.

Expression is inducible through the binding of a single class or multiple different classes of transcription factors to the several conditionally inducible elements; such binding positively affects transcription by the one or more promoters. The presence of the several silencer elements in close apposition to the several conditionally inducible elements suppresses transcriptional activity of at least one promoter in the expression vector as compared to that promoter's basal transcriptional activity in the absence of the silencer elements. Transcription of at least one downstream expressed region of the gene is thereby conditionally silenced.

Generally, the types and number of silencer elements, the types and number of conditionally inducible elements, their relative order and distance from each other in the silencer-inducible region, the type of promoter, and the closest distance between the silencer-inducible region and a promoter that is conditionally silenced thereby can be varied to increase the silencer-inducer ratio for the expression vector. This ratio for the same expression vector will probably vary according to the inducing condition and the linked promoter.

The role of silencer elements for repression of tissue-specific gene expression has been reviewed (Ogbourne and Antalis, 1998), but a conditional function for such elements has not been described previously. As disclosed herein, conditional silencing is a property of expression vectors constructed in accordance with the invention and is mechanistically novel. Functionally reversible silencing is defined for this purpose as a consequence of competition between at least one negative-acting transcription factor that binds to at least one of its cognate sites located in the silencer element, and at least one positive-acting transcription factor binding to at least one of its cognate sites located in the conditionally inducible element. Such competitive binding may occur at a common hybrid DNA binding site (Examples 1–3). Competition may also operate at a downstream site affecting transcription such as chromatin structure or at a TATA-box where transcription initiation complexes bind and the positive-acting or negative-acting factors usually exert their respective and independent control over transcription.

An expression vector may be further comprised of one or more splice donor and acceptor sites within an expressed region; a Kozak consensus sequence upstream of an expressed region for initiation of translation; downstream of an expressed region, multiple stop codons in the three forward reading frames to ensure termination of translation, one or more mRNA degradation signals, a termination of transcription signal, a polyadenylation signal, and a 3' cleavage signal. For expressed regions that do not contain an intron (e.g., a coding region from a cDNA), a pair of splice donor and acceptor sites may or may not be preferred. It would be useful, however, to include a mRNA degradation signal if it was desired to express one or more of the downstream regions only under the inducing condition. An origin of replication may be included that allows replication of the expression vector integrated in the host genome or as an autonomously replicating episome. Centromere and telomere sequences can also be included for the purposes of chromosomal segregation and protecting chromosomal ends from shortening, respectively. Random or targeted integration into the host genome is more likely to ensure maintenance of the expression vector but episomes could be maintained by selective pressure or, alternatively, may be preferred for those applications in which the expression vector is present only transiently.

The expression vector may also be engineered for genetic manipulation: for example, antibiotic resistance genes (e.g., amp$^r$, kan$^r$, tet$^r$); reporters or selectable markers (e.g., cat, DHFR, HSV-tk, lacZ, luc); polylinkers with multiple recognition sites for restriction endonucleases (e.g., BamHI, EcoRI, HindIII, NotI, SfiI); promoters for in vitro transcription (e.g., responsive to SP6, T3 or T7 bacteriophage polymerases); and primer annealing sites for in vitro replication.

A "silencer element" is an element of the expression vector that confers negative regulation on transcription of a downstream expressed region. Removal of the silencer element from an expression vector would be expected to increase basal expression of a downstream region. As described above, it may be present at least one, two, three, four, five, six, or more times as a homomultimer (i.e., repeats of the same silencer element) or as a heteromultimer (i.e., a mixture of different silencer elements or variations thereof) in the silencer-inducible region. Silencer elements (e.g., consensus sequences known in the art) are usually between about 8 and about 200 nucleotides in length. The silencer element may or may not be active in most cells (i.e., the silencer is active in decreasing gene expression in a cell specific manner in most cells, and under most conditions) but, preferably, it is active in decreasing gene expression even under non-inducing conditions of a conditionally inducible element present in the expression vector.

A "conditionally inducible element" is an element of the expression vector that confers positive regulation on transcription of a downstream expressed region under inducing conditions. It may be obtained from enhancer regions that are also conditionally inducible, but constitutively active enhancers that increase basal transcription under most or all conditions are not preferred sources for conditionally inducible elements. Removal of a conditionally inducible element from an expression vector would be expected to decrease expression of a downstream region under inducing conditions. As described above, it may be present at least one, two, three, four, five, six or more times as a homomultimer (i.e., repeats of the same conditionally inducible element) or a heteromultimer (i.e. a mixture of different conditionally inducible elements or variations thereof). Conditionally inducible elements (e.g., consensus sequences known in the art) are usually between about 4 and 100 nucleotides in length. The conditionally inducible element may or may not be active in most cells, but under non-inducing conditions, the latter situation is preferred. Examples of conditionally inducible elements include the hypoxia response enhancer (HRE) element, to which hypoxia inducible factor-1 (HIF-1) binds; HRE elements to which HIF-1α does not bind, for example, the metallothionein 1 (MT-I) and metallothionein II (MT-II) elements bound by metallothioncin transcription factor-1 (MTF-1) metal response elements; heat response elements; hormone response elements, NF-κB response elements; and growth factor response elements.

A "transcription factor" is a protein that specifically binds a cognate sequence found in silencer elements or conditionally inducible elements. Binding of a positively-acting transcription factor to its cognate site in a conditionally inducible element will increase expression; binding of a negatively-acting transcription factor to its cognate site in a silencer element will decrease expression. Such increases or decreases can be measured relative to the presence or absence of the transcription factor, or the presence or absence of an element in the expressed vector, under controlled reaction conditions. The presence or activity of the transcription factor may be dependent on the type of host cell or organism or the conditions under which that host is kept.

A "promoter" is responsible for basal expression of the downstream region in the expression vector. The promoter may or may not be active in most cells (e.g., gene expression is cell specific), but it should be active under the inducible condition of a silencer-inducible region included in the expression vector. The initiation of transcription from the promoter can be determined (e.g., by RACE or S1 nuclease protection techniques) and such initiation or even steadystate levels of stable transcripts are measures of promoter activity. Mutational analysis would be expected to confirm the boundaries and essential nucleotides of the promoter (e.g., binding, gel retardation, or protection by a basal transcription factor or RNA polymerase subunit is dependent on the existence or identity of a particular nucleotide in the promoter). The promoter may be obtained from a virus (e.g., an immediate early gene or long terminal repeat), a tissue specific eukaryotic gene, or a non-tissue specific eukaryotic gene (e.g., a house-keeping gene). The promoter may or may not be heterologous with respect to one or more of the silencer and conditionally inducible elements. There may be portions of the promoter that contribute to the function of the silencer-inducible region.

Spatial or temporal restricted expression may be desirable for some applications in which gene expression is targeted to a specific developmental stage or tissue, respectively. For example, such promoters may be used in expression vectors delivering an angiogenic growth factor to ischemic muscle or a deleterious gene to a solid tumor (Prentice and Webster 1995; Webster, 1999ab; Alexander et al., 1999). Regulatory elements in a tissue-specific promoter are usually bound by positive-acting transcription factors, therefore, their inclusion in an expression vector would have been expected to increase basal (i.e., uninduced) gene expression in the target tissue. This problem has been a limiting feature preventing the use of tissue-specific regulation in transgene regulation and gene targeting procedures. But the present invention eliminates this restriction because including a silencer element in the expression vector will conditionally silence the activity of tissue-specific promoter elements in the uninduced state and allow them to be active when induced.

Components of the expression vector may be derived from mammalian genes (e.g., adenine nucleotide transporter-2, albumin, aldehyde dehydrogenase-3, B29/Ig-β, cardiac actins or myosin heavy chains, CD95/Fas/APO1, crystallins, dopamine β-hydroxylase, elastase, endothelins, enolases, erythropoietin, 0fetoprotein, globins, glucocorticoid receptor, glutathione P transferase, growth hormone, heat shock proteins, heme oxygenase, histones, insulin, somatomedins, interferons, intestinal trefoil factor, metallothioneins, nuclear hormone receptors, phenylethanolamine N-methyltransferase, phosphoglycerate kinase, prostate specific antigen, protamines, pyruvate kinases, renins, SCG10, skeletal actins or troponins, sodium channel type II, synapsin, testis-specific histone H1t, thyroid receptor-β1, transferrin, tyrosine hydroxylase, vascular cellular adhesion molecule-1, von Willebrand factor); viruses (e.g., adenoviruses, adeno-associated virus, human cytomegalovirus, Epstein-Barr virus and other herpes simplex viruses, lentiviruses, Moloney leukemia or sarcoma virus, mouse mammary tumor virus, polyoma or SV40 virus, Rous sarcoma virus, vaccinia virus); and, less preferably, plant, insect, mold, fungal, and bacterial genes. See cited references for details on silencer and conditionally inducible elements, promoters, transcription factors, and their binding sites.

Expression of the downstream region can be induced by one or more conditional stimuli such as, for example, hyperthermia (e.g., temperature higher than about 39° C.), hypoxia (e.g., oxygen concentration lower than about 10%), inflammation (e.g., treating with LPS or inflammatory cytokines), ischemia (e.g., coronary artery ligation as shown in Prentice et al., 1997; femoral artery ligation as in Takeshita et al., 1994), oxidative stress (e.g., hypoxia reoxygenation of cardiac myocytes as shown in Webster, 1999b), growth stimulus, contractile function, antioxidants, and muscle fiber stretch.

Modulation of gene expression may be effected by affecting transcriptional initiation, transcript stability, translation of the transcript into protein product, protein stability, or a combination thereof. Quantitative effects can be measured by techniques such as in vitro transcription, in vitro translation, Northern hybridization, nucleic acid hybridization, reverse transcription-polymerase chain reaction (RT-PCR), run-on transcription, Southern hybridization, cell surface protein labeling, metabolic protein labeling, antibody binding, immunoprecipitation (IP), enzyme linked immunosorbent assay (ELISA), electrophoretic mobility shift assay (EMSA), radioimmunoassay (RIA), fluorescent or histochemical staining, microscopy and digital image analysis, and fluorescence activated cell analysis or sorting (FACS).

Gene expression can be assayed by use of a reporter or selectable marker gene whose protein product is easily assayed. Reporter genes include, for example, alkaline phosphatase, β-galactosidase (LacZ), chloramphenicol acetyltransferase (CAT), β-glucoronidase (GUS), bacterial/insect/marine invertebrate luciferases (LUC), green and red fluorescent proteins (GFP and RFP, respectively), horseradish peroxidase (HRP), β-lactamase, and derivatives thereof (e.g., blue EBFP, cyan ECFP, yellow-green EYFP, destabilized GFP variants, stabilized GFP variants, or fusion variants sold as LIVING COLORS fluorescent proteins by Clontech). Such reporter genes would use cognate substrates that are preferably assayed by a chromogen, fluorescent, or luminescent signal. Alternatively, assay product may be tagged with a heterologous epitope (e.g., FLAG, MYC, SV40 T antigen, glutathione transferase, hexahistidine, maltose binding protein) for which cognate antibodies or affinity resins are available. Examples of drugs for which selectable marker genes exist are ampicillin, geneticin (G418)/kanamycin/neormycin, hygromycin, puromycin, and tetracycline. An enzyme (e.g., diphtheria toxin, dihydrofolate reductase, HSV1 thymidine kinase) may be used as a selectable marker in sensitive host cells or auxotrophs. For example, diphtheria toxin can be used to ablate cell in lineage mapping; stepped increasing concentrations of methotrexate can increase the copy number of an expression vector linked to a DHFR selectable marker by gene amplification; gancyclovir can negatively select for a viral thymidine kinase selectable marker.

Techniques for measuring transcriptional or translational activity in vivo are known in the art. For example, a nuclear run-on assay may be employed to measure transcription of a reporter gene. The translation of the reporter gene may be measured by determining the activity of the translation product. The activity of a reporter gene can be measured by determining one or more of the abundance of transcription of polynucleotide product (e.g., RT-PCR of GFP transcripts), translation of polypeptide product (e.g., immunoassay of GFP protein), and enzymatic activity of the reporter protein per se (e.g., fluorescence of GFP or energy transfer thereof).

An "expressed region" may be derived from any gene and may be provided in either orientation with respect to the promoter; the expressed region in the antisense orientation will be useful for making cRNA, antisense, and RNA interference. The gene may be derived from the host cell or organism, from the same species thereof, or designed de novo; but it is preferably of archael, bacterial, fungal, plant, or animal origin. The gene may have a physiological function of one or more nonexclusive classes: structural proteins like albumin, amyloid, apolipoproteins, globins, sarcomere components, and transferrin; cytokines, hormones, and other soluble factors regulating cell growth, mitosis, meiosis, differentiation, and development; soluble and membrane receptors for such factors; adhesion molecules; cell-surface receptors and ligands thereof; cluster differentiation (CD) antigens, antibody and T-cell antigen receptor chains, histocompatibility antigens, and other mediators of immunity; chemokines, receptors thereof, and other factors involved in inflammation; enzymes producing lipid mediators of inflammation and regulators thereof; clotting and complement factors; ion channels and pumps; neurotransmitters, neutrophic factors, and receptors thereof; oncogenes, tumor suppressors, and other signal transducers; proteases and inhibitors thereof; catabolic or metabolic enzymes, and regulators thereof. Some genes produce alternative transcripts, encode subunits that are assembled as homopolymers or heteropolymers, or produce propeptides that are activated by protease cleavage.

As an example, the class of cytokines includes the following: 4-1BB ligand, amphiregulin, angiopoietin 1 to angiopoietin 4, APO3 ligand, BMP-2 to BMP-15, BDNF, betacellulin, cardiotrophin-1, CD27 ligand, CD30 ligand, CD40 ligand, CNTF, EGF, epiregulin, erythropoietin, Fas ligand, FGF-1 to FGF-19, Flt-3 ligand, G-CSF, GDF-1, GDF-3, GDF-8 to GDF-10, GITR ligand, GM-CSF, heparin binding-EGF, hepatocyte growth factor, IFN-α, IFN-βs, IFN-γ, IGF-I, IGF-II, inhibin A, inhibin B, IL-1α, IL-1β, IL-2 to IL-7, IL-9 to IL-11, IL-12 p35, IL-12 p40, IL-13 to IL-19, leptin, LIF, LIGHT, LT-β, lymphotactin, M-CSF, midkine, MIS, macrophage stimulating protein, neuregulin, NGF, NT-3, NT-4, NT-6, oncostatin M, OX40 ligand, PDGF-A, PDGF-B, placenta growth factor, pleiotrophin, SMDF, SCF, TALL-1, TALL-2, TGF-α, TNF-β1 to β3, thymopoietin, TNF-α, TNF-β, TRAIL, TRANCE, VEGF-A, VEGF-B, VEGF-C, VEGF-D, and VEGI. Most of these cytokines are ligands for one or more known receptors of high or low affinity; in contrast, a ligand of the HER2 receptor is not yet known. More information about these cytokines can be obtained from articles and references lists contained in Nicola (*Guidebook to Cytokines and Their Receptors*, Oxford Press, 1997); Thomson (*The Cytokine Handbook*, Academic Press, 1998); R&D Systems catalogs and its web site; and U.S. Pat. Nos. 5,773,252 and 5,985, 614.

Other enzymes and cellular proteins include adenosine deaminase, angiostatin, apoptosis inhibitor proteins (AIP1 or AIP2), BCL2 and MYC family members, catalase, chaperonins and heat shock proteins, cyclins, deoxyribonuclease, DMD2, DT- and NADPH-diaphorase, endostatin, endothelins, fumagillin, glutathione peroxidase, glutathione transferase, growth hormone, heat shock factor, insulin, hypoxanthine guanine phosphoribosyl transferase, kinases, matrix metalloproteinases (MMP-1, MMP-2, MMP-9, MT-1-MMP) and their inhibitors (TIMP-1, TIMP-2, TIMP-3, TIMP-4), nitric oxide synthases (iNOS or nNOS), phosphatases, proliferin, ribonucleases, superoxide dismutase, survivin, thymidine kinase, tissue plasminogen activator, and urokinase.

The downstream expressed region may encode a translational fusion. Open reading frames of regions encoding a polypeptide and at least one heterologous domain may be ligated in register. If a reporter or selectable marker is used as the heterologous domain, then expression of the fusion protein may be readily assayed or localized. The heterologous domain may be an affinity orepitope tag.

A polynucleotide may be ligated to a linker oligonucleotide or conjugated to one member of a specific binding pair (e.g., antibody-digoxygenin/hapten/peptide epitope, biotin-avidin/streptavidin, glutathione transferase or GST-glutathione, maltose binding protein-maltose, polyhistidine-nickel, protein A/G-immunoglobulin). The polynucleotide may be conjugated by ligation of a nucleotide sequence encoding the binding member. A polypeptide may be joined to one member of the specific binding pair by producing the fusion encoded such a ligated or conjugated polynucleotide or, alternatively, by direct chemical linkage to a reactive moiety on the binding member by chemical cross-linking. Such polynucleotides and polypeptides may be used as an affinity reagent to identify, to isolate, and to detect interactions that involve specific binding of a transcript or protein product of the expression vector. Before or after affinity binding of the transcript or protein product, the member attached to the polynucleotide or polypeptide may be bound to its cognate binding member. This can produce a complex in solution or immobilized to a support. A protease recognition site (e.g., for enterokinase, Factor Xa, ICE, thrombin) may be included between adjoining domains to permit site specific proteolysis that separates those domains and/or inactivates protein activity.

The amount of an expression vector administered to a mammalian cell or non-human mammal by transfection or transgenesis techniques, respectively, according to the invention is an amount effective to introduce the expression vector into host cells or non-germline tissues on a transient or stable basis (e.g., the expression vector can be detected in such cells or tissues at least one week after ceasing its administration). The vector can be maintained as an episome or may be integrated into a host chromosome. Thus, the term "effective amount" refers to that amount of composition necessary to achieve the indicated effect.

Pharmaceutical compositions that are useful in the methods of the invention may be administered in solid or liquid (especially to stabilize nucleic acids for storage and transportation), ophthalmic, suppository, aerosol, prolonged release, or other formulations. In addition to the expression vector, such compositions may contain pharmaceutically-acceptable carriers and vehicles, buffers, excipients, salts, stabilizers, preservatives, and other ingredients that enhance and facilitate drug administration. The composition may include such components, for example, as the following: nanospheres, microspheres, liposomes, defective or replicatively competent viral particles, chemical transfecting agents that condense nucleic acids, and a member of the antibody/ antigen, receptor/ligand (e.g., transferrin, galactosylated peptide), or other specific binding pairs that directs introduction of the expression vector to a target cell or tissue in preference to other cells or tissues.

Production of gene and cell products according to the present regulation will be regulated for good laboratory practices (GLP) and good manufacturing practices (GMP) by governmental agencies (e.g., U.S. Food and Drug Administration). This requires accurate and complete recordkeeping, as well as monitoring of QA/QC. Oversight of patient protocols by agencies and institutional panels is also envisioned to ensure that informed consent is obtained; the safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Another aspect of the invention is the use of expression vectors in applications such as, for example, gene therapy (e.g., therapeutic or prophylactic), production of recombinant biologicals, genetic diagnosis, drug screening, and genetic research (e.g., genomics, proteomics, in vivo and in vitro models of human disease).

The present invention may be used alone, or as an adjunct to standard medical or surgical treatments. "Treatment" as used herein refers to: reducing or alleviating the severity of symptoms in a mammal; lessening the number of symptoms; preventing symptoms from worsening or progressing; suppressing or eliminating infectious agents, autoimmune cells, and cancerous cells; preventing an infection or disease in a patient who is free therefrom; or combinations thereof. Treatment of cardiac disease, for example, may include reduction or prevention of ischemic damage, inhibition of restenosis, neutralization of other pathological effects of heart or vascular disease, diagnosis hypoxia, or combinations thereof.

In particular, at least six clinical trials are currently ongoing in which angiogenic growth factors, including VEGF and FGF genes, are being delivered with plasmid and adenovirus vectors to patients with ischemic heart disease and critical limb ischemia (see *Genetic Engineering News* Vol. 18, Number 17, October 1998; *Cardiology Today*, Vol 3, Number 1, January 2000). The goal is to stimulate angiogenesis and collateral vessel growth to treat ischemia. But these trials did not disclose the solution provided by the present invention to the problem of tightly regulating gene expression in the target tissue (Prentice and Webster, 1995; Webster, 1999ab; Alexander et al., 1999). Instead, constitutively active (CMV) promoters were used so the procedures are not sufficiently effective because of expression of the growth factor in other tissues. In the present invention, however, VEGF can be delivered to ischemic heart or limb muscles using conditionally silenced-hypoxia inducible expression vectors. Using the present invention, VEGF would be expressed at a low level of basal activity in healthy perfused tissue and at a high level of induced activity in ischemic tissue which is hypoxic (Lee et al., 2000), thereby confining angiogenesis to the target tissue and providing a safer and more effective treatment.

The amount of the composition which is administered to the patient is preferably an amount that does not induce any deleterious effects which outweigh the advantages which accompany its administration. Thus, treatment is preferably performed under supervision of a trained physician or with careful monitoring by a veterinarian.

Compositions of the present invention may be administered by any known route (e.g., enteral, parenteral, topical). Parenteral routes include intraarterial, intrabronchial, intramuscular, intrathecal, intravenous, subcutaneous or subdermal, transmucosal, and other injection or infusion techniques, without limitation. For example, compositions may be administered orally, parenterally, topically, regionally, or systemically Actual dosage levels of active ingredients in compositions may be varied so as to administer an amount of the expression vector that is effective to achieve the desired therapeutic or prophylactic effect in a particular patient. Thus, the selected dose will depend on the silencer-inducer ratio, choice of the downstream expressed region and its function, the size of the expression vector, the route of administration, the severity of the condition being treated, and the condition and prior medical history of the patient being treated.

It is also within the skill of the art, however, to start doses at levels lower than required to achieve the desired therapeutic or prophylactic effect and to gradually increase the dosage until the desired effect is achieved. These compositions may be administered according to the methods of the invention in a single dose (e.g., to treat acute disease or for stable transfection) or in multiple doses which are administered at different times (e.g., to treat chronic disease or for transient transfection). A dose of the composition may be repetitively administered to a patient (e.g., every few days to every few years), whereby gene expression is conditionally silenced and inducible after the initial treatment and then boosted by subsequent treatments.

But it would be understood as well that the specific dose for any particular patient will depend on a variety of factors, including body weight, gender, age, general health, diet, time and route of administration, combination with other drugs and patient treatments, and severity of the disease being treated. Unlike most active ingredients of pharmaceutical compositions, the range of effective amounts of expression vector would be low when the expression vector persists because it is replicated during cell division or maintained in the cell. Of course, the amount of the expression vector that is administered may be dependent upon other components of the composition and numerous factors understood by a person skilled in the art.

DNA is transcribed to produce an RNA transcript corresponding to the DNA, the RNA is translated to produce a nascent chain, and post-translationally processed (e.g., acetylation, acylation, amidation, disulfide bonding, glycosylation, phosphorylation, hydroxylation of γ-carboxyglutamic acid, methylation, phosphorylation, proteolysis, sulfatation) and folded. All of nascent chain, folded protein, and post-translationally processed protein are generically called polypeptide.

Gene activation may be achieved by inducing an expression vector containing a downstream region related to the host gene (e.g., the entire coding region or functional portions of the host gene, hypehporphic mutant versions thereof) or unrelated to the host gene that acts to relieve suppression of gene activation (e.g., at least partially inhibiting expression of a negative regulator of the host gene such as a soluble cytokine receptor). Overexpression of transcription or translation, as well as overexpressing protein function, is a more direct approach to gene activation. Alternatively, the down-stream expressed region may direct homologous recombination into a locus in the genome and thereby replace an endogenous transcriptional regulatory region of the host gene with the silencer-inducible region of the expression vector.

An expression vector may be introduced into the host mammalian cell or non-human mammal by a transfection or transgenesis technique using, for example, chemicals (e.g., calcium phosphate, DEAE-dextran, lipids, polymers), electroporation, naked DNA technology, microinjection, or viral infection; preferably, the introduced expression vector integrates into the host genome of the mammalian cell or non-human mammal. Many neutral and charged lipids, sterols, and other phospholipids to make lipid carrier vehicles are known. For example, neutral lipids are dioleoyl phosphatidyl-choline (DOPC) and dioleoyl phosphatidyl ethanolamine (DOPE); an anionic lipid is dioleoyl phosphatidyl serine (DOPS); and cationic lipids are dioleoyl trimethyl ammonium propane (DOTAP), dioctadecyldiamidoglycyl spermine (DOGS), diolebyl trimethyl ammonium (DOTMA), and 1,3-di-oleoyloxy-2-(6-carboxyspermyl)-propyl-amide tetra-acetate (DOSPER). Dipalmitoyl phosphatidylcholine (DPPC) can be incorporated to improve the efficacy and/or stability of delivery. FUGENE 6, LIPOFECTAMINE, LIPO-FECTIN, DMRIE-C, TRANSFECTAM, CELLFECTIN, PFX-1, PFX-2, PFX-3, PFX-4, PFX-5, PFX-6, PFX-7, PFX-8, TRANSFAST, TFX-10, TFX-20, TFX-50, and LIPOTAXI lipids are proprietary formulations. The polymer may be polyethylene glycol (PEG) or polyethylenimine (PEI); alternatively, polymeric materials can be formed into nano-spheres or microspheres. Naked DNA technology delivers the expression vector in plasmid form to a cell, where the plasmid may or may not become integrated into the host genome, without using chemical transfecting agents (e.g., lipids, polymers) to condense the expression vector prior to introduction into the cell.

Thus, a mammalian cell may be transfected with an expression vector; also provided are transgenic non-human mammals. In the previously discussed alternative, a homologous region from a host gene can be used to direct integration of the silencer-inducible region to a particular genetic locus in the host genome and thereby regulate expression of the host gene at that locus. Polypeptide may be produced in vitro by culturing transfected cells; in vivo by transgenesis; and ex vivo by introducing the expression vector into allogeneic, autologous, histocompatible, or xenogeneic cells and then transplanting the transfected cells into a host organism. Special harvesting and culturing protocols will be needed for transfection and subsequent transplantation of host stem cells into a host mammal. Immunosuppression of the host mammal post-transplant and encapsulation of the host cells may be necessary to prevent rejection.

The expression vector may be used to replace function of an absent or totally defective host gene, supplement function of a partially defective host gene, or compete with activity of the host gene. Thus, the cognate gene of the host may be neomorphic, hypomorphic, hypermorphic, or normal. Replacement or supplementation of function can be accomplished by the methods discussed above, and transfected mammalian cells or transgenic non-human mammals may be selected for high expression (e.g., assessing amount of transcribed or translated produce, or physiological function of either product) of the downstream region. But competition between the expressed downstream region and a neomorphic, hypermorphic, or normal host gene may be more difficult to achieve unless the encoded polypeptides are multiple subunits that form into a polymeric protein complex. Alternatively, a negative regulator or a single-chain antibody that inhibits function intracellularly may be encoded by the downstream region of the expression vector. Therefore, at least partial inhibition of functional host genes may require using antisense, RNA interference, or ribozyme technology in which the expression vector contains a downstream region corresponding to the unmodified antisense transcript, either or both strands of a dsRNA or a ribozyme, respectively.

Antisense polynucleotides were initially believed to directly block translation by hybridizing to mRNA transcripts, but is now thought to involve degradation of mRNA transcripts of a viral or cellular gene. The antisense molecule may be made using at least one functional portion of a gene in the antisense orientation as downstream expressed region in the expression vector.

RNA interference by dsRNA appears to involve enzymatic cleavage because the mRNA transcripts are converted to fragments of about 20–25 ribonucleotides through a process different from antisense inhibition (possibly by degradation with ribonuclease D). The latter is preferred because of its greater efficiency and ease of design (e.g., antisense oligonucleotides often need to be chemically synthesized with modified nucleotides to increase their half-life). dsRNA can be made from a portion of the coding region of a cellular or viral gene of at least 25 nucleotides with the two ssRNA strands being produced by the same or different expression vectors, at least one of which contains a downstream region in antisense orientation.

Ribozymes catalyze specific cleavage of an RNA transcript or genome. The mechanism of action involves sequence-specific hybridization to complementary cellular or viral RNA, followed by endonucleolytic cleavage. The ribozyme includes one or more sequences complementary to the subject RNA as well as catalytic sequences responsible for RNA cleavage (e.g., hammerhead, hairpin, axehead motifs). For example, potential ribozyme cleavage sites within a subject RNA are initially identified by scanning the subject RNA for ribozyme cleavage sites which include the following trinucleotide sequences: GUA, GUU and GUC. Once identified, an oligonucleotide of between about 15 and about 20 ribonucleotides corresponding to the region of the subject RNA containing the cleavage site can be evaluated for predicted structural features, such as secondary structure, that can render candidate oligonucleotide sequences unsuitable. The suitability of candidate sequences can then be evaluated by their ability to hybridize and cleave cellular or viral RNA.

Any disease may be treated with the present invention if the genetic basis and an inducer associated with the disease are known (e.g., inflammation and other stress conditions, ischemia and other hypoxic conditions, fluctuation of glucose concentration or other metabolic disorders).

Genetic vaccination may be used to provide a model of human disease or for immunomodulation in an afflicted patient (e.g., induction, stimulation, potentiation, or suppression of the immune response) by expressing or inhibiting the expression of allergens, autoantigens, antigens of infectious agents (e.g., cell surface or virus capsid/coat antigens), and tumor antigens. See U.S. Pat. Nos. 5,580,859, 5,589,466, 5,697,901, 5,804,566, 5,830,877, 5,849,719, 5,985,847, and WO 98/20734. Antibody directed against the antigen may also be produced for diagnostic, therapeutic, or prophylactic use. Thus, a downstream region may encode an immunogenic portion of one or more such antigens as single or multivalent epitopes. It is preferred that the antigen be expressed as a fusion protein with a cytokine that acts as an adjuvant (e.g., IFN-γ, GM-CSF).

Tissues which may be targeted include the nervous system (e.g., brain, eye, glia, central and peripheral nerves); the reticuloendothelial system (e.g., blood, bone marrow, dendritic cells, erythroid cells, granulocytes, lymph vasculature endothelium, lymphocytes, megakaryocytes and platelets, monocytes and macrophages, myeloid cells, neutrophils, spleen, thymus); the endocrine, reproductive, and urinary systems (e.g., adrenal gland, breast, kidney, ovary, pituitary gland, prostate, testicle, thyroid gland, uterine endothelium); the cardiopulmonary system (e.g., heart, lung, arterial and venous vascular endothelium); the digestive system (e.g., colon, gall bladder, large and small intestines, liver, pancreas, rectum, stomach); bone, cartilage, connective tissues, skin, smooth muscle, and striated muscle; ectodermal, endodermal, or mesodermal tissues; mesenchymal and parenchymal tissues.

The ability to introduce the expression vector into a variety of normal cells and tissues suggests that the treatment of benign and malignant cancers (e.g., ascites and solid tumors, carcinomas, leukemias, lymphomas, melanomas, sarcomas) is possible. Some tumor types of interest are breast, colorectal, lung, ovarian, pancreatic, prostatic, renal, and testicular carcinoma.

Thus, examples of diseases that might be treated by regulated gene expression of an appropriate coding region, transcribed region in antisense orientation, dsRNA, or ribozyme, or that may provide models of such disease, are the following: acquired or inherited immunodeficiency, allergy and other immune hypersensitivities, anemia and thalassemia, autoimmune disease, hemolytic or septic shock, hemophilia, inflammation and other stress conditions, ischemia and other hypoxic conditions, carcinoma (e.g., basal cell, basosquamous, Brown-Pearce, ductal, Ehrlich tumor, in situ, Krebs, Merkel cell, small or non-small cell lung, oat cell, papillary, bronchiolar, squamous cell, transitional cell, Walker), leukemia (e.g., B-cell, T-cell, HTLV, acute or chronic lymphocytic, mast cell, myeloid), histiocytoma, histiocytosis, Hodgkin disease, non-Hodgkin lymphoma, plasmacytoma, reticuloendotheliosis, adenoma, adenocarcinoma, adenofibroma, adenolymphoma, ameloblastoma, angiokeratoma, angiolymphoid hyperplasia with eosinophilia, sclerosing angioma, angiomatosis, apudoma, branchioma, malignant carcinoid syndrome, carcinoid heart disease, carcinosarcoma, cementoma, cholangioma, cholesteatoma, chondrosarcoma, chondroblastoma, chondrosarcoma, chordoma, choristoma, craniopharyngioma, chrondroma, cylindroma, cystadenocarcinoma, cystadenoma, cystosarcoma phyllodes, dysgerminoma, ependymoma, Ewing sarcoma, fibroma, fibrosarcoma, giant cell tumor, ganglioneuroma, glioblastoma, glomangioma, granulosa cell tumor, gynandroblastoma, hamartoma, hemangioendothelioma, hemangioma, hemangiopericytoma, hemangiosarcoma, hepatoma, islet cell tumor, Kaposi sarcoma, leiomyoma, leiomyosarcoma, leukosarcoma, Leydig cell tumor, lipoma, liposarcoma, lymphangioma, lymphangiomyoma, lymphangiosarcoma, medulloblastoma, meningioma, mesenchymoma, mesonephroma, mesothelioma, myoblastoma, myoma, myosarcoma, myxoma, myxosarcoma, neurilemmoma, neuroma, neuroblastoma, neuroepithelioma, neurofibroma, neurofibromatosis, odontoma, osteoma, osteosarcoma, papilloma, paraganglioma, paraganglioma nonchromaffin, pinealoma, rhabdomyoma, rhabdomyosarcoma, Sertoli cell tumor, teratoma, theca cell tumor, and other diseases in which cells have become dysplastic, immortalized, or transformed.

The following examples are meant to be illustrative of the present invention, however practice of the invention is not limited or restricted in any way by them.

EXAMPLES

Art-known techniques are described in books and manuals like Ausubel et al. (*Current Protocols in Molecular Biology*, Wiley, 1999); Birren et al. (*Genome Analysis Series*, CSHL, 1997–1999); Bonifacino et al. (*Current Protocols in Cell Biology*, Wiley, 1999); Carey and Smale (*Transcriptional Regulation in Eukaryotes*, CSHL, 2000); Coligan et al. (*Current Protocols in Immunology*, Wiley, 1999); Coligan et al. (*Cunent Protocols in Protein Science*, Wiley, 1999); Dracopoli et al. (*Current Protocols in Human Genetics*, Wiley, 1999); Harlow and Lane (*Using Antibodies*, CSHL, 1999); Hogan et al. (*Manipulating the Mouse Embryo*, CSHL, 1994); Marshak et al. (*Strategies for Protein Purification and Characterization*, CSHL, 1996); Murphy and Carter (*Trangenesis Techniques*, Humana, 1993); Murray (*Gene Transfer and Expression Protocols*, Humana Press, 1991); Pinkert (*Trangenic Animal Technology*, Academic, 1994); Robbins (*Gene Therapy Protocols*, Humana, 1996); Sambrook et al. (*Molecular Cloning*, CSHL, 1989); Spector et al. (Cells, CSHL, 1998); Tuan (*Recombinant Gene Expression Protocols*, Humana, 1997); and Walther and Stein (*Gene Therapy of Cancer*, Humana, 2000).

Sources of reagents, techniques for construction of expression vectors, culture and transfection of cells, determination of gene expression, and binding studies are described in Webster et al. (1993), Bodi et al. (1995), Wu et al. (1996), Prentice et al. (1997), Hu et al. (1998), Discher et al., (1998), Discher et al. (1999), and Webster et al. (1999).

Plasmid vectors suitable for evaluating the transcriptional activity of silencer elements, conditionally inducible elements, and promoters, alone or in combination, by detection of a firefly luciferase reporter gene are available from Promega. Such vectors include a transcriptional pause site, a polylinker upstream of the coding region for luciferase, a polyadenylation signal from SV40 following the luciferase coding region, E. coli and f1 origins of replication, and the selectable marker amp$^r$. pGL3 basic vector (pGL3BV) lacks eukaryotic promoter, silencer, and enhancer sequences. In comparison to the basic vector, the pGL3 enhancer vector also lacks a eukaryotic promoter but contains an SV40 enhancer downstream of the luciferase coding region and a polyadenylation signal; the pGL3 promoter vector (pGL3PV) contains an SV40 early promoter upstream of the luciferase coding region, and allows the insertion of one or more silencer-inducible regions into the Kpnl restriction enzyme site as shown in the figures. The pGL3 control vector contains both the SV40 promoter upstream of the coding region and the SV40 enhancer downstream of the coding region.

Silencer-inducible regions were cloned into pGL3PV, pMHC164 (Molkentin et al., 1996), pMHC86 (Prentice et al., 1997), pMHC1.2, and pHSA150. As shown in FIG. 1, pMHC164 was made by ligating a rat αcardiac myosin heavy chain (αMHC) promoter (i.e., −164 to +16 fragment) into pGL3-BV cut with SmaI and HindIII. Similarly, pMHC86 was made by inserting a SmaI-HindIII fragment (i.e., −86 to +16 αMHC promoter) into pGL3-BV, pMHC1.2 was made by inserting a SmaI-HindIII fragment (i.e., −1200 to +16 αMHC promoter) into pGL3BV, and pHSA150 was made by inserting a SmaI-HindIII fragment (i.e., −150 to +239 human skeletal actin promoter) into pGL3BV.

BRIEF DESCRIPTION OF SEQUENCES

SEQ ID NO:1 HRE (S) 5'-TGTCACGTCCTGCACGAC-GTA-3' is the sequence of the oligonucleotide containing the hypoxia response enhancer (HRE) element from the human phosphoglycerate kinase gene in the sense orientation (HRE is also designated HREpgk).

SEQ ID NO:2 SIL (S) 5'-CTTCAGCACCGCGGACAG-TGCC-3' is the sequence of the oligonucleotide containing the silencer (SIL) element from the human synapsin gene in the sense orientation.

SEQ ID NO:3 HREpgk-M (S) 5'-TGTCCATTCCTGCA-CGACGTAC-3' is the sequence of the oligonucleotide containing a mutated HREpgk element in the sense orientation.

SEQ ID NO:4 SIL-M (S) 5'-CTTCAGCACCGCTTACA-GTGCC-3' is the sequence of the oligonucleotide containing a mutated SIL element in the sense orientation.

SEQ ID NO:5 [SIL/HRE]1 5'-CTTCAGCACCGCGGAC-AGTGCCTGTCACGTCCTGCACGACGTA-3'

SEQ ID NO:6 [SIL/HRE]2 5'-CTTCAGCACCGCGGAC-AGTGCCTGTCACGTCCTGCACGACGTACTTCAG-CACCGCGGACAGTGCCTGTCACGTCCTGCACGA-CGTA-3'

SEQ ID NO:7 [SIL/HRE]3 5'-CTTCAGCACCGCGGAC-AGTGCCTGTCACGTCCTGCACGACTTCAGCAC-CGCGGACAGTGCCTGTCACGTCCTGCACGACT-TCAGCACCGCGGACAGTGCCTGTCACGTCCTG-CACGACGGTAC-3' (continuous but no overlap)

SEQ ID NO:8 [SIL/HRE]1 5'-CTTCAGCACCGCGGAC-AGTCACGTCCTGCACGA-3' (with five base overlap)

SEQ ID NO;9 [SILO/HRE3] 5'-CTTCAGCACCGCTTA-CAGTGCCTGTCACGTCCTGCAGGACGTACTTCA-GCACCGCTTACAGTGCCTGTCACGTCCTGCACG-ACGTACTTCAGCACCGCTTACAGTGCCTGTCAC-GTCCTGCACGACGTA-3' (the silencer element is mutated in this oligonucleotide)

SEQ ID NO:10 [SIL/HREm]1 5'-CTTCAGCACCGCG-GACAGTGCCTGTCCATTCCTGCACGACGTACTT-CAGCACCGCGGACAGTGCCTGTCCATTCCTGC-ACGACGTACCTTCAGCACCGCGGACAGTGCCT-GTCCATTCCTGCACGACGTAC-3'

SEQ ID NO:11 [SIL/NFκB]3 5'-CTTCAGCACCGCGG-ACAGTTGAGGGGACTTTCCCAGGCTTCAGCAC-CGCGGACAGTTGAGGGGACTTTCCCAGGCTTC-AGCACCGCGGACAGTTGAGGGGACTTTCCCAG-GCGTAC-3'

SEQ ID NO:12 [SILM/NFκB]3 5'-CTTCAGCACCGCTT-ACAGTTGAGGGGACTTTCCCAGGCTTCAGCAC-CGCTTACAGTTGAGGGGACTTTCCCAGGCTTCA-GCACCGCTTACAGTTGAGGGGACTTTCCCAGGC-GTAC-3'

SEQ ID NO:13 [SIL/NFκB]1 5'-CTTCAGCACCGCGG-ACAGTTGAGGGGACTTTCCCAGG-3'

SEQ ID NO:14 [SIL/MRE]3 5'-CTTCAGCACCGCGG-ACAGTTGAGCTTCGGGGCTTTTGCACTCGTCCC-GGCTCTACTTCAGCACCGCGGACAGTTGAGCT-TCGGGGCTTTTGCACTCGTCCCGGCTCTACTTC-

AGCACCGCGGACAGTTGAGCTTCGGGGCTTTTG-
CACTCGTCCCGGCTCTA-3'
SEQ ID NO:15 HREet-1 5'-CTGGCCTTATCTCCGGCT-
GCACGTTGCCTGTTGGTGACTAATMCACMTAA-3'
is the sequence of the oligonucleotide containing the hypoxia response enhancer (HRE) element from the endothelin (ET-1) gene.

In each of the above sequences, the first silencer element is shown in bold. For each sequence, only the sense strand is shown but it should be understood that the anti-sense strand was also synthesized. The sense and antisense strands were then annealed before cloning into a construct with appropriate cohesive end(s).

EXAMPLE 1

Conditional Silencing and Position Dependence

Figure 2A:
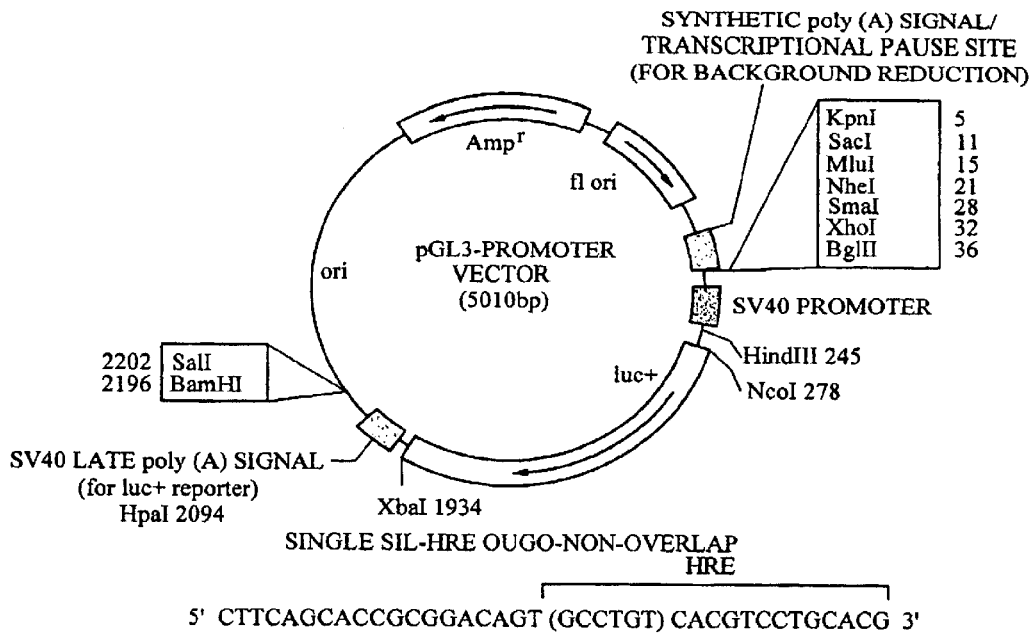
FIG. 2A depicts construction of the pGL3PV HRE/SIL series of expression vectors with no overlap between silencer and conditionally inducible elements (SEQ ID NOS:5–7, each of which includes SEQ ID NO:17 as shown).
Figure 2B:
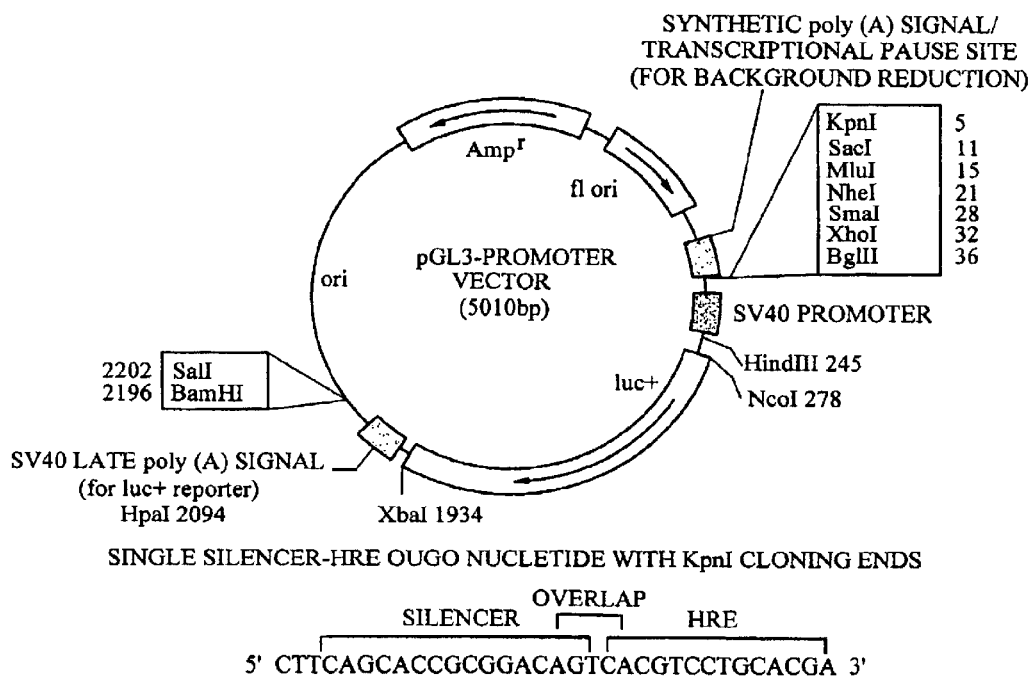
FIG. 2B depicts construction of the pGL3PV HRE/SIL expression vector with five base overlap (SEQ ID NO:8) between silencer and conditionally inducible elements.

Silencer-inducer regions containing one, two, or three copies each of a silencer (SIL) element from the human synapsin gene and a conditionally inducible (HRE) element from the phosphoglycerate kinase gene (described above as SEQ ID NOS:5–7) were cloned into the Kpnl restriction enzyme site of pGL3PV as shown in FIG. 2A. These constructs are referred to as pGL3-[SIL/HRE]1, pGL3-[SIL/HRE]2, and pGL3-[SIL/HRE]3. In addition, pGL3-[SIL/HRE]3 (with overlap) was constructed by cloning three copies of an oligonucleotide (SEQ ID NO:8) into the Kpnl restriction enzyme site of pGL3PV as shown in FIG. 2B. pGL3-[SIL0/HRE3] was constructed using an oligonucleotide (SEQ ID NO:9) cloned into the Kpnl restriction enzyme site of pGL3PV. Here, the critical bases for binding of transcription factor to the SIL element have been mutated so that the oligo-nucleotide still contains three HRE elements. This construct serves as a control for the SIL element.

All of these plasmid constructs were made with the inserted oligonucleotide positioned in both 5' to 3' (S) and 3' to 5' (AS) orientations, and then verified by sequencing (Discher et al., 1999). Results shown below are for the non-overlapping pGL3-[SIL/HRE] series in the (S) configuration (SEQ ID NOS:5–7). There was no difference between S and AS insert orientation, nor was there any significant difference between the non-overlap and the overlap silencer-inducer regions (three copies of SEQ ID NO:8).

Purified expression vectors (Discher et al., 1998) as indicated in the Tables were transfected into cell lines (e.g., skeletal muscle C2C12, HeLa, and cardiac myocytes) by calcium phosphate or lipid transfection (Webster et al., 1993; Discher et al., 1998). In all cases, transfection efficiency was normalized using an internal control (Renilla luciferase from Promega) and equal amounts of protein extract were used for the reporter assays. Three to four days after transfection, cells were maintained and continuously exposed to aerobic conditions (21% $O_2$/5% $CO_2$ air) or hypoxic conditions (1% $O_2$/5% $CO_2$/balance $N_2$) for 24 hr. Other conditions for exposing cells to hypoxia have been described (Webster and Bishopric 1992; Webster et al., 1993; Discher et al., 1998; Webster et al., 1999). Briefly, cells are placed in an air-tight environmental chamber with a temperature, humidity, and gas controlled environment, with a standard gas mixture of 1% $O_2$/5% $CO_2$/balance $N_2$. The system includes continuously recording oxygen electrode, pH meter, and a CELL-TRAK motion analysis system to record changers in cell motion and shape. All cell manipulations take place inside the chamber to avoid reoxygenation. Cells were harvested, lysed, and assayed for expression of the reporter (luc) gene after treatments (Discher et al., 1998; Webster et al., 1999). Table 1 shows the results of two experiments with duplicate samples using C2C12 skeletal myocytes exposed to hypoxia for 20 hr in each case; luciferase activity normalized to protein concentration is shown.

TABLE 1

| Expression Vector | Ratio Under Hypoxic Conditions |
| --- | --- |
| PGL3-[SIL0/HRE3] | 8.9 ± 1.6 |
| PGL3-[SIL/HRE]1 | 17.7 ± 3.1 |
| PGL3-[SIL/HRE]2 | 79.0 ± 6.4 |
| PGL3-[SIL/HRE]3 | 189.5 ± 11.9 |

The silencer-inducer ratio can be seen to increase in a linear manner under hypoxic conditions, with the number of SIL and HRE elements being increased from one copy to three copies of each. It is concluded from this example that both insert series using SEQ ID NOS:5–8 mediate hypoxia-reversible silencing. The magnitude of this effect is directly proportional to the number of SIL/HRE elements and overlap between the individual SIL and HRE elements is not necessary for conditional silencing.

Further studies focused on the pGL3-[SIL/HRE]3 expression vector for which expression of the luciferase reporter was studied in detail for C2C12 skeletal myocytes (n=12), cardiac myocytes (n=6), and HeLa cells (n=8). The silencer-inducer ratios are shown in Table 2. The silencer-inducer ratio was highest in C2C12 skeletal myocytes.

TABLE 2

| Cell Type | Ratio Under Hypoxic Conditions |
| --- | --- |
| Skeletal Myocyte | 533 ± 12.7 |
| Cardiac Myocyte | 52 ± 12 |
| HeLa Cell | 247 ± 24 |

Conditional silencing requires that repression of gene expression be selective for the non-induced state (e.g., basal expression under aerobic conditions). The impact of silencing on reporter gene expression from pGLPV-[SIL/HRE]3 in transfected C2C12 cells cultured under non-inducing (aerobic) or inducing (hypoxic) conditions are shown in Table 3 as ratios of pGLPV-[SIL/HRE]3: pGLPV-[SIL0/HRE3].

TABLE 3

| Aerobic Repression pGLPV-[SIL/HRE]3: pGLPV-[SIL0/HRE3] | Hypoxic Repression pGLPV-[SIL/HRE]3: pGLPV-[SIL0/HRE3] |
| --- | --- |
| 2.8 | 62 |

Silencing with 3X SIL elements reduced expression under aerobic conditions to 2.8% relative to the corresponding non-silenced construct whereas expression under hypoxia remained at 62%, indicating that hypoxia significantly reversed this silencing. The extent of reversal of silencing under hypoxia is related to the amount of HIF-1 transcription factor produced and the affinity of the HRE binding site (see below).

These results demonstrate conditional silencing for constructs containing oligo-nucleotide inserts including SEQ ID NOS:5–8 in C2C12 cells. These constructs all contain pairs of SIL and HRE elements within 50 bp of each other. To determine whether the close proximity of the elements was important, three SIL elements without an HRE (SEQ ID NO:10) were cloned into the DrawIII71045 restriction enzyme site about 500 bp upstream of the multicloning site of pGL3PV and three HRE elements without an SIL element (SEQ ID NO:9) were cloned into the Kpnl restriction enzyme site of the same vector. Both were inserted in the sense 5'-3' orientation. The resulting construct is called pGL3PV3XSIL///3XHRE. Expression was measured under either aerobic or hypoxic conditions, and compared with pGLPV[SIL/HRE]3. The results are shown in Table 4.

TABLE 4

| pGLPV [SIL/HRE]3 Aerobic | pGLPV [SIL/HRE]3 Hypoxic | pGL3PV3XSIL/// 3XHRE Aerobic | pGL3PV3XSIL/// 3XHRE Hypoxic |
|---|---|---|---|
| 0.28 | 100 | 0.42 | 11.6 |

The results in Table 4 show that when the SIL elements were widely separated from the inducible HRE elements reversal of silencing by hypoxia was less. This resulted in a significantly lower silenced-inducer ratio (357 for the SIL/HRE coupled construct and 27.6 for the SIL/HRE separated construct). It should, however, be noted that conditional silencing was still apparent with pGL3PV3XSIL///3XHRE indicating that activation of the inducible factor was able to reduce silencing even when the factors have widely separated binding sites. This indicates more than one mechanism of conditional silencing; the first associated with competitive binding to the hybrid DNA binding site and the second (in this instance, a weaker effect) acting independently of the relative positions of the SIL and HRE elements. The involvement of competition of transcription factors for the hybrid DNA binding site is supported by direct binding assays.

EXAMPLE 2

Conditional Silencing with a Tissue-Specific Promoter

The results described in Tables 1–4 confirm that conditional silencing occurs when SIL and HRE elements were incorporated into the pGLPV vector. This vector uses the SV40 early promoter which is not tissue specific. To determine whether the same effects could be observed using a tissue-specific promoter, the SV40 promoter region of pGL3PV was replaced with a −164 bp sequence containing the promoter of the cardiac-selective α-MHC promoter as described in FIG. 1. Constructs containing SILO/HRE3, [SIL/HRE]2, and [SIL/HRE]3 were made. These were each transfected into cardiac myocytes and the expression of luciferase was measured under aerobic conditions and 24 hr after treatment with hypoxia as described above. The results are shown in Table 5.

Although the silencer-inducer ratio was less in cardiac myocytes than in C2C12 cells, substitution of the SV40 early promoter with the α-MHC promoter did not change the enhancement indicating that conditional silencing was effective using either a non-tissue-specific or a tissue-specific promoter. Note that the presence of SIL elements augmented the silencer-inducer ratio by approximately 10-fold in Table 5.

TABLE 5

| Expression Vector | Ratio Under Hypoxic Conditions |
|---|---|
| pMHC164-luc | 0.67 |
| pMHC164-[SIL0/HRE3] | 4.2 |
| pMHC164-[SIL/HRE]2 | 10.4 |
| pMHC164-[SIL/HRE]3 | 52.3 |

EXAMPLE 3

Conditional Silencing with Multiple Inducers

These studies demonstrate that conditional silencing occurred in three different cell types, was not dependent on the type of promoter used, and involves at least two distinct mechanisms one involving competition of silencer and inducible factors for a hybrid/linked DNA binding site, and one independent of the relative position of the elements. All of these studies involved HRE elements as the conditionally inducible elements which bind instrinsic factors. To determine whether the effect could be extra-polated to other inducible conditions, parallel constructs were made in which the HRE elements were substituted with an NFκB element. The NFκB factor is induced by inflammatory mediators including lipopolysaccharide (LPS). To make these constructs, oligonucleotides containing NFκB-SIL elements (SEQ ID NO:11) and NFκB-SIL-mutant elements (SEQ ID NO:12) were cloned into the Kpnl restriction enzyme site of pGL3PV to produce pGL3-[SIL/NFκB]3 and pGL3-[SILO/NFκB3], respectively. To evaluate conditional silencing, these constructs were transfected into a macrophage cell line called RAW 264.7 obtained from the American Type Culture Collection (ATCC, Bethesda, Md.) and cultured in MEM with fetal bovine serum as recommended by ATCC. Cells were transfected with each vector using calcium phosphate as described above. After transfection, confluent cultures were serum starved for 3 days and then left untreated for an additional day or treated with 3 μg/ml (final concentration) of LPS (Sigma) shown to activate the intrinsic factor NFκB. The expression of luciferase was measured in extracts from induced (LPS treated) and un-induced cultures exactly as described above. The silencer-inducer ratios (with LPS:without LPS) are shown in Table 6 and demonstrate conditional silencing.

TABLE 6

| pGL3-[SIL0/NFκB3] Ratio | pGL3-[SIL/NFκB]3 Ratio |
|---|---|
| 4.31 ± 0.6 | 24.3 ± 2.2 |

It can be seen from Table 6 that the induction of expression through the NFκB element increases from 4.3 to 24.3 by inclusion of silencer elements. This was accomplished by repression of the uninduced expression by>90%and reversal of this repression to about 45% by LPS activation. Reversal of silencing in this system was not as efficient as treatment by hypoxia in the HRE/SIL system described above. Nevertheless the system clearly demonstrates a similar conditional silencing effect.

The results demonstrate conditional silencing using hypoxia or LPS as the inducing stimulus and HRE/SIL and NFκB/SIL elements respectively positioned within 50 bp of each other. To directly address the possibility that steric hinderance and binding site competiton may play roles in this effect we measured the binding of proteins to SIL/HRE (SEQ ID NO:5) and SIL/NFκB (SEQ ID NO:13) double-stranded oligonucleotides using the gel electrophoretic mobility shift assay (GEMSA). Preparing nuclear extracts, labeling oligonucleotides, binding conditiona, and electrophoresis have been previously described (Wu et al., 1998). These conditions were employed in all binding assays used here except that 0.2% NP40 was included in the binding cocktail and 4% polyacrylamide gels were used for electrophoresis. C2C12 cells were used for the SIL/HRE assays and RAW 264.7 for SIL/NFκB assays.

Figure 3A:
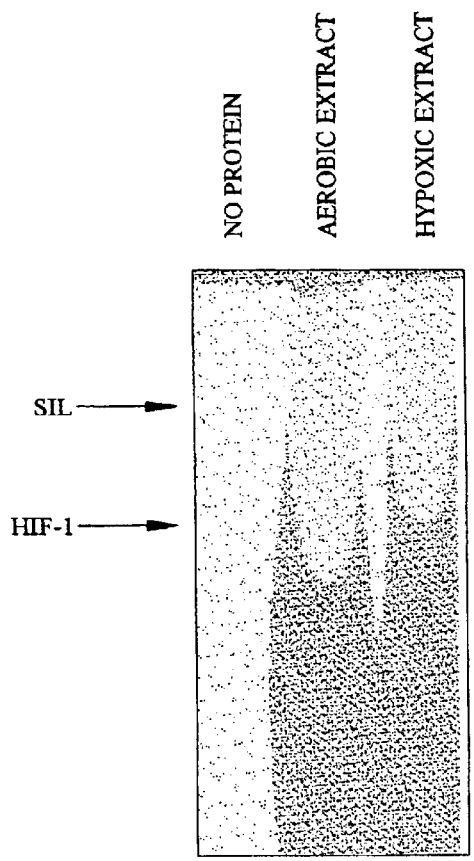
FIGS. 3A–3B depict GEMSA analysis of HIF-I and NFκB transcription factor binding to cognate sites with or without induction.
Figure 3B:
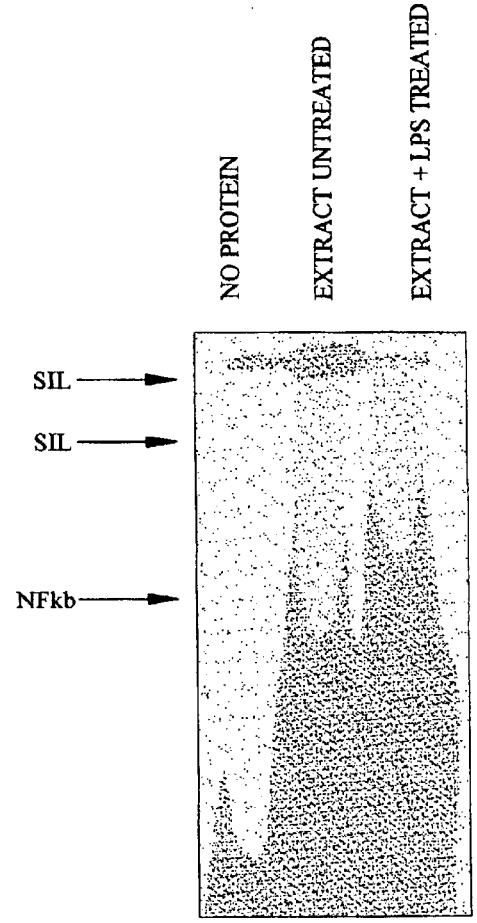

Briefly, the protocol was as follows. Cultures of C2C12 and RAW macrophages were grown to confluence in MEM with 10% serum. Cultures were serum starved for 2 days and nuclear extracts were prepared (un-induced). Parallel plates were made hypoxic for 24 hr (C2C12) or treated with 3 μg/ml LPS for 40 min (RAW). These plates were harvested and used to prepare nuclear extracts (induced). Equal amounts of proteins were mixed with equal amounts of $^{32}$P-labeled oligonucleotide probes and binding was allowed to occur for 40 min at 21° C. Complexes were separated in by 4% PAGE at 200 V/room temperature. The results are shown in FIGS. 3A and 3B. The arrows in FIG. 3A indicate positions of binding of intrinsic factors: Silencer and HIF-1 transcription factors. The specificities of these shifted bands were confirmed by competition assays as described previously (Wu et al., 1997; Hu et al., 1998; Murphy et al., 1999).

Binding of the HRE and Silencer binding factors in these in vitro reactions were not optimal because the silencer requires 0.1% NP40 for efficient binding, but this NP-40 concentration inhibits HIF-1 binding. Therefore it was necessary to compromise and use 0.05% NP40. Even though the specific binding of both Silencer and HRE factors was weak it is clear that binding of the silencer element is reduced when reactions used nuclear extracts from hypoxia-activated cells containing HIF-1 (lane 2 compared with lane 3). The effect was more pronounced using the SIL/NFκB hybrid oligonucleotide and the RAW±LPS extracts. In this case binding of the SIL binding protein can be clearly seen when using extracts from untreated cells; however extracts from cells treated with LPS showed strong activation of NFκB binding and almost complete elimination of the binding of the SIL element. These results demonstrate that HRE binding factors and NFκB can displace SIL binding factor from oligonucleotides containing linked elements within 50 bp of each other. This result supports a role for steric hinderance and competition for a common hybrid binding site as one of the mechanisms for conditional silencing as described herein.

EXAMPLE 4

Conditional Silencing in Vivo

To determine whether there was silencing of these constructs in tissue in vivo, rat hearts were injected with pGLPV-[SIL/HRE]3 or pGLPV-[SIL0/HRE3] and expression was measured after 5 days. Surgical procedures, DNA injection into the left ventricle, tissue preparation, and reporter assay were performed as previously described (Prentice et al., 1997). The results from two experiments normalized to 100 for the non-silenced construct are shown in Table 7.

TABLE 7

| PGLPV-[SIL0/HRE3] | PGLPV-[SIL/HRE]3 |
|---|---|
| 100 | 14 ± 6 |

The only difference between these constructs is the presence or absence of functional silencer elements, therefore the results strongly support the presence of silencing in vivo. Experiments in progress are measuring the ischemia-reversibility of this silencing.

To determine whether conditional silencing occurred in vivo, a rat ischemic hindlimb model was used (Takeshita et al., 1994). In this model, the rat hindlimb muscle was made ischemic by ligating and removing the femoral and associated arteries, then vector DNA was injected directly into the muscle. After an appropriate period, the muscles were isolated and reporter gene expression was measured as described above. Briefly, the protocol is as follows. Rats were anesthetized and a skin incision was made on the right limb to expose the femoral artery. After separating the artery from the vein, the proximal end of the femoral and the distal portion of the saphenous artery were ligated. Approximately 2 cm of the artery between the ligatures, including all side-branches, was dissected free and excised. Blood flow to the calf was monitored using a laser doppler surface analyzer (Lisca). For the sham control, the same procedure was used on the left limb but the arteries were left intact. Cesium chloride-purified DNA (1 μg/μl) was injected directly into the area of muscle between the ligatures in four injections of 25 μl each. Similar injections were made to the sham operated limb muscle. The overlying skin was closed with a surgical stapler and the animals were allowed to recover. One to two days later, rats were sacrificed with a lethal dose of sodium pentobarbital, and the injected muscles were dissected out and transferred to ice-cold PBS. The results of one set of experiments (n=2) is shown in Table 9. Blood flow to the foot was 77ml/min (n=2) before removal of the femoral artery. After removal, the flow was reduced to<5 ml/min, a greater than 95% loss.

TABLE 9

| pGLPV-[SIL0/HRE3] Ischemia/Sham ratio | pGLPV-[SIL/HRE]3 Ischemia/Sham ratio |
|---|---|
| 1.43 | 21.3 |

Induction of the control construct (un-silenced) by ischemia was low in these experiments because the rat hindlimb develops collateral circulation rapidly and the muscles become repefused (and reoxygenated). However it can be seen that the presence of silencers mediated a 20-fold increase in the silencer-inducer ratio confirming that conditional silencing occurs with these constructs in vivo.

EXAMPLE 5

Therapeutic Impact of Hypoxia/Silencer-activated Genes.

Exposure of cardiac myocytes to hypoxia for 24 hr and reoxygenation for 20 hr (conditions that simulate myocardial ischemia-reperfusion) causes the death by apoptosis of>30% of the myocytes (Webster et al., 1999). This model was used to determine whether a hypoxia-activated gene (e.g., DT-diaphorase) that was silenced under aerobic conditions could protect cardiac myocytes from the oxidative stress caused by hypoxia-reoxygenation. DT-diaphorase is an anti-oxidant that mediates quenching of free radicals that are generated by quinone cycling during mitochondrial electron transport. A cDNA insert encoding DT-diaphorase was removed from a pcDNA vector with HindIII. The about 1.3 Kb insert was cloned into the HindIII-XbaI restriction enzyme sites of pGLPV-[HRE/SIL]3 after removing the luciferase cDNA insert. This required a two-step process: first, ligate at the HindIII restriction enzyme site and, second, fill in the remaining cohesive ends and blunt end circularize. Orientation was determined by sequencing. The construct is called pPV[SIL/HRE]3-DT-d. Cardiac myocytes were transfected with 2 μg of a CMV-green fluorescent protein (GFP, Clontech) and 8 μg of pPV[SIL/HRE]3-DT-d or empty vector as the control. The GFP is used to track transfected cells. Transfected cultures were exposed to hypoxia-reoxygenaton to cause 30% cell apoptosis as previously described (Webster et al., 1999). Parallel cultures were treated with 1% $H_2O_2$ to induce oxidative stress without hypoxia. After treatments, cultures were treated with Hoechst stain to identify apoptotic cells as described previously (Webster et al., 1999; Dougherty et al., 2000) and the same cells were examined with a fluorescent microscope to identify transfected GFP-positive cells. GFP-positive apoptotic and non-apoptotic cells were counted to determine whether cotransfection of pPV[SIL/HRE]3-DT-d, which will be induced during hypoxia, would protect against apoptosis caused by reoxygenation. The results from these experiments (n=2) are shown in Table 10.

TABLE 10

| Control/GFP Apop − (%) | Control GFP Apop + (%) | pPV[SIL/HRE] 3-DT-d Apop − (%) | pPV[SIL/HRE] 3-DT-d Apop + (%) |
|---|---|---|---|
| 76 ± 13 | 24 ± 6 | 96 ± 21 | 8 ± 3 |

Cells transfected with pPV[SIL/HRE]3-DT-d were strongly protected against apoptosis caused by 24 hr hypoxia and 20 hr reoxygenation. Control cultures transfected with empty vector diplayed 24% apoptosis of GFP-positive cells after reoxygenation, which is similar to our previous results (Webster et al., 1999). Cultures cotransfected with pPV[SIL/HRE]3-DT-d displayed only 8% GFP-positive apoptosis positive cells indicating protection of>60% (p<0.05). Cells treated with $H_2O_2$ showed the same rate of apoptosis (~9%) regardless of the cotransfected plasmid. Therefore the activation of DT-diaphorase expression and reversal of the conditionally silenced vector during the hypoxia phase is able to affect cardioprotection during subsequent reoxygenation. This shows that a conditionally silenced gene can be activated by a disease phenotype (hypoxia) and made to exert a therapeutic effect on the targeted host cells subjected to a disease (reperfusion injury).

Other genes were cloned into pGL3PV-[SIL/HRE]3 for expression by conditional silencing using SEQ ID NO:7, and then sequenced. The β-gal cDNA with a hema gluttinin (HA) epitope tag was cut from pcDNA3.1/HisB/lacZ (Invitrogen) using HindIII and XbaI. The about 4 Kb insert was cloned into the HindIII-XbaI restriction enzyme sites of pGL3PV-[SIL/HRE]3 after removing the luciferase CDNA insert. This construct is called pβ-gal[SIL/HRE]3. A human VEGF121 cDNA was cloned by PCR from cDNA of human smooth muscle cells. Primers with HindIII and XbaI restriction enzyme sites at the ends were used and the purified product was cloned into the HindIII-XbaI restriction enzyme sites of pGL3PV[SIL/HRE]3 as previously described. This construct is called pVEGF121[SIL/HRE]3. Full length human HIF-1α cDNA cut from pBluescript (Stratagene) was cut and then cloned into the XbaI-NcoI restriction enzyme sites of pGL3PV-[SIL/HRE]3. This construct is called pHIF-1α[SIL/HRE]3.

Hypoxia-activated expression of β-gal, IGF-1, VEGF, and HIF-1α was demonstrated. In the case of pHIF-1α[SIL/HRE]3, it was shown that cotransfection of this construct into C2C12 cells with pGLPV-[SIL/HRE]3 enhanced hypoxia-mediated conditional silencing by about 10 fold. This suggest the use of this vector to augment conditional silencing in other contexts. This effect may be particularly advantageous in cells and tissues with lower HIF-1α production.

TRE/SIL1 (SEQ ID NO:16) 5'-CTTCAGCACCGCGGA-CAGTTGACACGATCACCTCCCATTAAGGAGAG-AGATCTCCTTCAGCACCGCGGACAGTTGACACG-ATCACCTCCCATTAAGGAGAGAGATCTCCTTCA-GCACCGCGGACAGTTGACACGATCACCTCCCA-TTAAGGAGAGAGATCTC-3' TRE is a conditionally inducible element from the thyoxin gene.

Anti-oxidant response elements are contained in the AND (P)H quinone reductase gene (Jaiswal, 1994) and has consensus sequence 5'-TGACNNNGC-3'; metal response elements are contained in metallothionein genes (Murphy et al., 1999); heat response elements are contained in heat shock genes like HSP70 and HSP82. Hormone response elements are a class including androgen response elements (ARE), glucocorticoid response elements (GRE), and estrogen response elements (ERE). NFκB responsive elements are contained in interferon and other cytokine genes and have consensus sequences as shown in SEQ ID NOS:11 and 13.

References

Agha-Mohammadi and Lotze (2000) J Clinical Investigation, 105:1177–1183
Alexander et al. (1999) Clinical Experimental Pharmacology Physiology, 29:661868
Baniahmad et al. (1997) Molecular Cellular Biology, 17:4259–4271
Barath et al. (1999) J Biological Chemistry, 274:3378–3384
Bessis et al. (1997) Proc Natl Acad Sci USA, 94:5906–5911
Bodi et al. (1995) Cardiovascular Research, 30:975–984
Burcin et al. (1997) Molecular Cellular Biology, 17:1281–1288
Cavazzano-Calvo et al. (2000) Science, 288:669–672
Discher et al. (1998) J Biological Chemistry, 273:26087–26093
Discher et al. (1999) Biotechniques, 26:1026–1030
Freundlieb et al. (1999) J Gene Medicine, 1:4–12
Hu et al. (1998) Biochemical Biophysical Research Communications, 245:894–899
Jaiswal (1994) Biochemical Pharmacology, 28:339444
Jhaveri and Morrow (1998) Biochim Biophys Acta, 1396:179–190
Kay et al. (2000) Nature Genetics, 24:257–261
Lee andGross (1993) Molecular Cellular Biology, 13:727–738
Lee et al. (2000) New England J Medicine, 342:626–633
Li et al. (1993) Proc Natl Acad Sci USA, 90:1460–1464
Malone et al. (1997) Proc Natl Acad Sci USA, 94:12314–12319
Malone et al. (2000) J Immunology, 164:2550–2556
Millecamps et al. (1999) Nature Biotechnology, 17:865–869
Molkentin et al. (1996) J Molecular Cellular Cardiology, 28:1211–1225

Murphy et al. (1999) Cancer Research, 59:1315–1322
Nagasawa et al. (1997) Molecular Cellular Endocrinology, 130:153–165
Nourbakhsh and Hauser (1997) Immunobiology, 198:65–72
Nourbakhsh and Hauser (1999) EMBO J, 18:6415–6425
Nourbakhsh et al. (1993) EMBO J, 12:451459
Ogbourne and Antalis (1998) Biochemical J, 331:1–14
Osada etal. (1997) J Biochemistry, 121:355–363
Osada et al. (1999) Biochemical J, 342:189–198
Prentice and Webster (1995) Mol Cell Biology Human Diseases Series, 5:281–300
Prentice et al. (1997) Cardiovascular Research, 35:567–574
Quinn (1996) Progress Neurobiology, 50:363–379
Schoenherr and Anderson (1995) Science, 267:1360–1363
Takeshita et al. (1994) Circulation, 90 (suppl II):228–234
Thrower et al. (1996) J Virology, 70:91–100
Weber et al. (1997) J Neuroscience, 17:7583–7593
Webster (1999a) The Scientist, 13:13
Webster (1999b) Gene Therapy, 6:951–954
Webster and Bishopric (1992) J Molecular Cellular Cardiology, 24:741–751
Webster et al. (1993) J Biological Chemistry, 268:16852–16859
Webster et al. (1999) J Clinical Investigation, 104:239–252
Wolfe and Grimes (1999) J Cellular Biochemistry, 75:555–565
Wolfe et al. (1999) Biology Reproduction, 61:1005–1011
Ye et al. (1999) J Biological Chemistry, 274:26661–26667

All publications, patent applications, and patents cited in this specification are incorporated by reference in their entirety where they are cited. Such references are also cited as indicative of the skill in the art.

While the invention has been described in connection with what is presently considered to be practical and preferred embodiments, it should be understood that it is not to be limited or restricted to the disclosed embodiments but, on the contrary, is intended to cover various modifications, substitutions, and combinations within the scope of the appended claims. In this respect, one should also note that the protection conferred by the claims is determined after their issuance in view of later technical developments and would extend to all legal equivalents.

Therefore, it is to be understood that variations in the invention that are not described herein will be obvious to a person skilled in the art and could be practiced without departing from the invention's novel and non-obvious elements with the proviso that the prior art is excluded. For example, art-known silencer elements, conditionally inducible elements, promoters, genes that are transcribed by the expression vector, other components of the expression vector, intrinsic factors, transfection techniques, infection techniques, transgenesis techniques, and other methods for making or using the expression vector can be substituted for those described above. Similarly, the expression vector's nucleotide sequence, orientation and separation of components, and selection of those components may be varied and the utility of the variation determined by comparing the effect on basal expression, the silencer-inducer ratio, spatial or temporal pattern of regulated expression, or combinations thereof.

What is claimed is:

1. An isolated expression vector comprising (a) a silencer-inducible region comprising at least one hypoxia response enhancer element and at least one neuron restrictive silencer element that binds neuron restrictive silencer factor and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic.

2. An isolated expression vector comprising (a) a silencer-inducible region comprising at least one hypoxia response enhancer element and at least one neuron restrictive silencer element from the human synapsin gene and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other, wherein expression of the at least one nucleotide sequence is silenced when the vector is incorporated in a non-hypoxic cell and the silenced expression is reversed when the cell is made hypoxic.

3. An isolated expression vector comprising (a) a silencer-inducible region comprising at least one hypoxia response enhancer element and at least one neuron restrictive silencer element that comprises the sequence of SEQ ID NO:2 and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic.

4. An isolated expression vector comprising (a) a silencer-inducible region comprising at least one hypoxia response enhancer element from the human phosphoglycerate kinase gene and at least one neuron restrictive silencer element that binds neuron restrictive silencer factor and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic.

5. An isolated expression vector comprising (a) a silencer-inducible region comprising at least one hypoxia response enhancer element that comprises the sequence of SEQ ID NO:1, and at least one neuron restrictive silencer element that binds neuron restrictive silencer factor and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic.

6. An isolated expression vector comprising (a) a silencer-inducible region comprising at least one hypoxia response enhancer element that binds hypoxia inducible factor-1, and at least one neuron restrictive silencer element that binds neuron restrictive silencer factor and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other, wherein expression of the at least one nucleotide sequence is silenced when the vector is incorporated in a non-hypoxic cell and the silenced expression is reversed when the cell is made hypoxic.

7. An isolated expression vector comprising (a) a silencer-inducible region comprising at least one hypoxia response enhancer element and at least one neuron restrictive silencer element that binds neuron restrictive silencer factor and (b) a viral promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic.

8. An isolated expression vector comprising (a) a silencer-inducible region comprising at least one hypoxia response enhancer element and at least one neuron restrictive silencer element that binds neuron restrictive silencer factor and (b) a mammalian promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic.

9. An isolated expression vector comprising (a) a silencer-inducible region comprising at least one hypoxia response enhancer element and at least one neuron restrictive silencer element that binds neuron restrictive silencer factor and (b) a cell-type specific promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic.

10. An isolated expression vector comprising (a) a silencer-inducible region comprising at least one hypoxia response enhancer element and at least one neuron restrictive silencer element that binds neuron restrictive silencer factor and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other,
wherein expression of the at least one nucleotide sequence is silenced when the vector is incorporated in a non-hypoxic cell and the silenced expression is reversed when the cell is made hypoxic, and
wherein the nucleotide sequence is a functional coding region of a gene selected from the group consisting of adenosine deaminase, angiopoietin, apoptosis inhibitor protein, angiostatin, B-cell CLL/lymphoma, catalase, deoxyribonuclease, DT-diaphorase, endostatin, erthropoeitin, fibroblast growth factor, fumagillin, β-globin, glutathione peroxidase, granulocyte-colony stimulating factor, granulocyte macrophage-colony stimulating factory, heat, shock transcription factor, hepatocyte growth factor, interferon, tissue metalloproteinase inhibitor, nitric oxide synthase, platelet derived growth factor, proliferin, somatomedin C, superoxide dismutase, survivin, thymidine kinase, tissue plasminogen activator, tumor protein p53, urokinase, and vascular endothelial growth factor.

11. An isolated expression vector comprising (a) a silencer-inducible region comprising at least one hypoxia response enhancer element and at least one neuron restrictive silencer element that binds neuron restrictive silencer factor and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other, wherein expression of the at least one nucleotide sequence is silenced when the vector is incorporated in a non-hypoxic cell and the silenced expression is reversed when the cell is made hypoxic, and wherein the expression vector further comprises one or more sequences selected from the group consisting of a Kozak sequence, a transcription termination sequence, a polyadenylation sequence and a mRNA degradation sequence.

12. An isolated expression vector comprising (a) a silencer-inducible region comprising at least one hypoxia response enhancer element and at least one neuron restrictive silencer element that binds neuron restrictive silencer factor and (b) a promoter upstream of at least one nucleotide sequence and in operable linkage with and regulated by the silencer-inducible region, the at least one neuron restrictive silencer element and at least one hypoxia response enhancer element being arranged within 500 nucleotides of each other, wherein expression of the at least one nucleotide sequence is silenced when the vector is incorporated in a non-hypoxic cell and the silenced expression is reversed when the cell is made hypoxic; and wherein the expression vector is encapsulated within an Adeno-Associated Virus particle.

13. An isolated expression vector comprising (a) a siliencer-inducible region comprising at least one NF-κB responsive element and at least one neuron restrictive silencer element that binds neuron restrictive silencer factor and (b) a promoter upstream of at least one nucleotide sequence and in operable linkage with and regulated by the silencer-inducible region, wherein the at least one neuron restrictive silencer element and at least one NF-κB responsive element are arranged within 500 nucleotides of each other, wherein expression of the at least one nucleotide sequence is silenced when the vector is incorporated in a cell subjected to a condition that results in NF-κB binding to the NF-κB responsive element, and the silenced expression is reversed when the condition is removed from the cell.

* * * * *